(12) United States Patent
Takenaka et al.

(10) Patent No.: US 8,889,349 B2
(45) Date of Patent: Nov. 18, 2014

(54) METHOD FOR TESTING MICROORGANISM OR THE LIKE AND TESTING APPARATUS THEREFOR

(75) Inventors: Kei Takenaka, Kashiwa (JP); Hideki Nakamoto, Tokai (JP); Kazuo Takei, Tokai (JP); Masahiro Kurihara, Yokohama (JP); Yuusuke Watanabe, Hitachinaka (JP); Hisao Saito, Tokyo (JP); Yasuhiko Sasaki, Tsuchiura (JP)

(73) Assignee: Hitachi Engineering & Services Co., Ltd., Ibaraki (JP)

( * ) Notice: Subject to any disclaimer, the term of this patent is extended or adjusted under 35 U.S.C. 154(b) by 97 days.

(21) Appl. No.: 12/914,055

(22) Filed: Oct. 28, 2010

(65) Prior Publication Data

US 2011/0104685 A1   May 5, 2011

(30) Foreign Application Priority Data

Oct. 30, 2009   (JP) ................. 2009-249647

(51) Int. Cl.
| | | |
|---|---|---|
| *C12Q 1/68* | (2006.01) | |
| *C12Q 1/02* | (2006.01) | |
| *C12Q 1/04* | (2006.01) | |
| *C12Q 1/06* | (2006.01) | |
| *G01N 1/30* | (2006.01) | |
| *G01N 21/64* | (2006.01) | |
| *G01J 3/36* | (2006.01) | |
| *G01J 3/44* | (2006.01) | |

(52) U.S. Cl.
CPC .... *G01N 21/6428* (2013.01); *G01N 2021/6441* (2013.01); *G01J 3/36* (2013.01); *G01N 2021/6421* (2013.01); *G01N 21/645* (2013.01); *G01J 3/4406* (2013.01)
USPC ................. 435/6.1; 435/29; 435/34; 435/39; 435/40.51

(58) Field of Classification Search
None
See application file for complete search history.

(56) References Cited

U.S. PATENT DOCUMENTS 5,047,321 A  *  9/1991  Loken et al. ................. 435/6.11
5,229,265 A  *  7/1993  Tometsko .................... 435/6.11

(Continued)

FOREIGN PATENT DOCUMENTS

| JP | 2000-342300 | 12/2000 |
| JP | 2008-157829 | 7/2008 |
| JP | 2009-178078 | 8/2009 |

OTHER PUBLICATIONS

Auty et al. Applied and Environmental Microbiology. 2001. 67(1): 420-425.*

(Continued)

*Primary Examiner* — Robert T Crow
*Assistant Examiner* — Joseph G Dauner
(74) *Attorney, Agent, or Firm* — Antonelli, Terry, Stout & Kraus, LLP.

(57) ABSTRACT

A method for accurately counting desired cells or microorganisms (viable bacteria) in a sample fluid in which contaminants are included is provided. One or plural types of membrane-permeable fluorochromes whose fluorescence amount is amplified by binding to a nucleic acid and glycerin are added to a sample fluid containing cells or microorganisms to be counted and allowed to stand for a certain time. Glycerin is added before or after or simultaneously with the mixing of the sample fluid and the fluorochrome(s). The cells or microorganisms to be counted are counted by staining the cells or microorganisms to be counted, followed by irradiating with light having a specific wavelength to detect the fluorescence emitted from the cells or microorganisms.

4 Claims, 18 Drawing Sheets

(56) References Cited

U.S. PATENT DOCUMENTS

| | | | |
|---|---|---|---|
| 5,830,668 A * | 11/1998 | Mordechai et al. | 435/7.4 |
| 2002/0055134 A1 * | 5/2002 | Fleming et al. | 435/32 |
| 2008/0153153 A1 | 6/2008 | Takenaka et al. | |
| 2009/0291488 A1 | 11/2009 | Takenaka et al. | |
| 2010/0093072 A1 | 4/2010 | Takenaka et al. | |
| 2010/0273208 A1 | 10/2010 | Takenaka et al. | |

OTHER PUBLICATIONS

SYTO Green Fluorescent Nucleic Acid Stains (retrieved on Dec. 7, 2011 from the Internet: <URL: http://probes.invitrogen.com/media/pis/mp07572.pdf >).*

LDS 751 (retrieved on Dec. 12, 2011 from the Internet: <URL: http://products.invitrogen.com/ivgn/product/L7595>).*

Gardiner et al. Applied and Environmental Microbiology. 2000. 66(6): 2605-2612.*

Propidium Iodide Nucleic Acid Stain (retrieved on Dec. 7, 2011 from the Internet: <URL: http://probes.invitrogen.com/media/pis/mp01304.pdf >).*

Strothkamp et al. Journal of Chemical Education. 1994. 71(1): 77-79.*

Kozjak-Pavlovic et al. PLoS Pathogens. 2009. 5(10): e1000629.*

Mitotracker Mitochondrion-selective Probes (retrieved on Dec. 13, 2011 from the Internet: <URL: http://probes.invitrogen.com/media/pis/mp07510.pdf>).*

Gregori et al. Applied and Environment Microbiology, Oct. 2001, p. 4662-4670.*

Lonza (retrieved on Feb. 26, 2014 from the internet: http://bio.lonza.com/uploads/tx_mwaxmarketingmaterial/Lonza_ManualsProductInstructions_SYBR_Green_II_Nucleic_Acid_Gel_Stain_-_Protocol.pdf).*

* cited by examiner

Fig. 5

|  | Type of fluorescence ||
| --- | --- | --- |
|  | Fluorescence of fluorochrome 1 | Fluorescence of fluorochrome 2 |
| V/K bacteria | ○ | ○ |
| Pigment particle of fluorochrome 1 | ○ | × |
| Pigment particle of fluorochrome 2 | × | ○ |

Fig. 9

| | Type of fluorescence | | | |
|---|---|---|---|---|
| | Blue (V/K bacteria) | Orange (killed bacteria / chromatophore) | Red (mitochondria / chloroplast) | Near-infrared (V/K bacteria) |
| Viable bacteria | ○ | × | × | ○ |
| Killed bacteria | ○ | ○ | × | ○ |
| Chloroplast | × | × | ○ | ○ |
| Chromatophore | × | ○ | ○ | × |
| Mitochondria | ×~○ | × | ○ | △~○ |
| Starch | ○ | ○ | ○ | ○ |
| Cellulose | ○ | ○ | ○ | ○ |
| Glycogen | ○ | ○ | ○ | ○ |
| Particle of blue cyanine fluorochrome for V/K bacteria | ○ | × | × | × |
| Particle of orange cyanine fluorochrome for killed bacteria | × | ○ | × | × |
| Particle of red fluorochrome for mitochondria | × | × | ○ | × |
| Particle of near-infrared cyanine fluorochrome for V/K bacteria | × | × | × | ○ | ic or the like and a testing apparatus therefor, and
METHOD FOR TESTING MICROORGANISM OR THE LIKE AND TESTING APPARATUS THEREFOR

BACKGROUND OF THE INVENTION

1. Field of the Invention

The present invention relates to a method for testing microorganisms or the like and a testing apparatus therefor, and particularly relates to a microorganism-testing apparatus using a fluorescent cytometry method. For the purpose of the present specification, the microorganism-testing method and the testing apparatus therefor refer to a method for testing cells or microorganisms and an testing apparatus therefor and are not intended to be limited to a method for testing only microorganisms and an testing apparatus therefor. For simplicity of indication, the "cells or microorganisms" may be simply indicated with "microorganisms" in the present specification and what is claimed is, in which case the "microorganisms" shall include the "cells".

2. Background Art

Viable bacteria-counting apparatuses (microorganism-testing apparatuses) are provided on the market which are intended for the speed-up and simplification of counting viable bacteria in a food. Among these, attention has been given to viable bacteria-counting apparatuses using fluorescent cytometry method as viable bacteria-counting apparatuses excellent in rapidity and quantitativity. Fluorescent cytometry methods are methods involving counting fluorescently-stained viable bacteria on a one-by-one basis in a short time and roughly classified into a fluorescent image cytometry method and a fluorescent flow cytometry method. The fluorescent image cytometry method is a method which involves adsorbing fluorochrome-stained viable bacteria onto a glass, filter, or the like and counting the adsorbed viable bacteria on a one-by-one basis. On the other hand, the fluorescent flow cytometry method is a method which involves making the flow diameter of a sample fluid containing fluorochrome-stained viable bacteria thin to count the viable bacteria flowing through a passage on a one-by-one basis.

A problem in measuring the number of viable bacteria in a food with the viable bacteria-counting apparatus using fluorescent cytometry is the requirement of purification for removing contaminants before counting. Contaminants include killed bacteria and particles of a fluorochrome used for staining in addition to materials derived from the food such as chloroplasts, chromatophores, mitochondria, carbohydrates (starch and glycogen), and a lipid mass. These contaminants contribute to the miscounting thereof as viable bacteria because they emit autofluorescence or fluorescence by being stained by, or adsorbing to, a fluorochrome. Methods for purifying viable bacteria include a centrifugation method and a column method, and these methods can separate viable bacteria and contaminants with a high purification degree.

In contrast, as an example of discriminating between viable bacteria and contaminants without performing purification, there is a method which involves discriminating between viable bacteria and killed bacteria using two types of fluorochromes to count viable bacteria. This method is a discrimination method based on the fact that although damage is present on the membrane surface of killed bacteria, damage is absent on the membrane surface of viable bacteria, and involves discriminating between viable bacteria and killed bacteria using a membrane-permeable blue fluorochrome, DAPI (4', 6-diamidine-2'-phenylindole), and a membrane-impermeable red fluorochrome, PI (propidium iodide). The blue fluorescence of DAPI is emitted from the viable bacteria and the killed bacteria because the membrane-permeable DAPI permeates the membrane of bacteria with or without damage, while the red fluorescence of PI is emitted only from the killed bacteria because the membrane-impermeable PI permeates only the damaged membrane thereof. A method involving specifically staining materials with a plurality of fluorochromes having different wavelengths to discriminate between the materials based on the difference in the wavelength between their fluorescences as in the above method is called a multi-staining method.

JP Patent Publication (Kokai) Nos. 2008-157829 A and 2009-178078 A disclose fluorescent flow cytometry methods using a technique involving holding a sample and a reagent(s) in a microorganism-testing chip to simply test microorganisms.

SUMMARY OF THE INVENTION

In a microorganism-testing apparatus, it is important to discriminate between viable bacteria and contaminants contained in a sample fluid to improve the accuracy of bacteria counts. There are some problems in improving the accuracy of bacteria counts.

A first problem for discriminating between viable bacteria and contaminants is that the fluorescence intensity of the viable bacteria is weak since the viable bacteria have an insufficient degree of fluorescent staining. To promote the degree of fluorescent staining, a chelating agent such as a surfactant and EDTA is known to be added as a staining promoter to the sample fluid in addition to a fluorochrome. However, the surfactant has a problem that it converts viable bacteria to killed bacteria because of its bactericidal properties and a problem that it has foaming properties and thus the generated foams disturb measurement. On the other hand, EDTA has a problem that it converts viable bacteria to killed bacteria because of its bactericidal properties and a problem that it increases environmental load at disposal because of its no biodegradability.

A second problem for discriminating between viable bacteria and contaminants is that a contaminant is present which is difficult to discriminate because of its same wavelength and fluorescence intensity as the fluorescence of any of the viable bacteria. Giving the above-described double staining with DAPI and PI as an example, viable bacteria emit only the blue fluorescence of DAPI; however, particles of DAPI also emit only blue fluorescence. It is difficult to discriminate between viable bacteria and DAPI particles because particles are also present which emit fluorescence having a intensity comparable to that of the fluorescence of the viable bacteria. The problem of discrimination between the viable bacteria and the pigment particles is not a problem limited to DAPI, but also holds true for using a different fluorochrome.

Meanwhile, as a method for accurately separating a desired species of bacteria from a detergent and paper chippings which are contained in a sample fluid and emit fluorescence, a method is known which involves doubly staining specific bacteria by use of two types of phages having micro DNAs (about 200 kb) stained by fluorochromes having different wavelengths (see JP Patent Publication (Kokai) No. 2000-342300 A). Even when the detergent and paper chippings which emit fluorescence are contained in the sample fluid, this method enables the specific bacteria to be discriminated from the detergent and paper chippings because the specific bacteria emit two types of fluorescences. This method enables measurement results to be obtained with very high precision when a specific species of bacteria is intended to be counted, but is not suitable for applications where all viable bacteria need to be counted irrespective of their species as in food inspection. No consideration is also given to the fluorochrome itself forming a contaminant.

A third problem for discriminating between viable bacteria and contaminants is that use of many types of fluorochromes for multi-staining increases the overlap of fluorescence spectra of fluorochromes, which makes it difficult to discriminate viable bacteria using the information of fluorescence. A general fluorescence cytometer identifies viable bacteria and concomitants by excluding the overlap of fluorescence spectra through analysis, which requires a high-performance analyzer, increasing production cost.

A first object of the present invention is to provide a microorganism-testing method and a testing apparatus, in a microorganism-testing method for counting cells or microorganisms (viable bacteria) by staining the cells or microorganisms with a fluorochrome, capable of reducing the problems of bactericidal properties, foaming properties, and biodegradability and promoting the fluorescent staining of the cells or microorganisms to measure the cells or microorganisms.

A second object of the present invention is to provide a microorganism-testing method and a testing apparatus, in counting cells or microorganisms (viable bacteria), capable of suppressing a reduction in the accuracy of counting the cells or microorganisms due to a fluorochrome with which the cells or microorganisms are stained.

A third object of the present invention is to provide a microorganism-testing method and a testing apparatus, also in a microorganism test using a multi-staining method, capable of improving the accuracy of counting viable bacteria (cells) without using a high-performance analyzer.

To achieve the first object, the present invention is adapted to count desired cells or microorganisms (viable bacteria) by adding a membrane-permeable fluorochrome whose fluorescence amount is amplified by binding to a nucleic acid and glycerin as a fluorescence promoter to a sample fluid containing the cells or microorganisms to stain the cells or microorganisms, irradiating the stained cells or microorganisms with light having a specific wavelength, and detecting the fluorescence emitted from the cells or microorganisms.

Glycerin can be added before or after or simultaneously with the mixing of the sample fluid and the fluorochrome.

It is preferable to ensure that the final concentration of the mixture of the sample fluid and glycerin is within 1% to 30%.

To achieve the second object, the present invention is also adapted to count desired cells or microorganisms (viable bacteria) by adding two or more membrane-permeable fluorochromes with different fluorescence spectra, whose fluorescence amount is amplified by binding to a nucleic acid, to a sample fluid containing the cells or microorganisms to stain the cells or microorganisms, irradiating the stained cells or microorganisms with lights having specific wavelengths, and detecting fluorescences having different emission spectra, emitted from the cells or microorganisms.

The two or more fluorochromes preferably have peaks of the respective fluorescence spectra at least 50 nm away from each other.

The present invention is also adapted to count desired cells or microorganisms (viable bacteria) by adding a membrane-permeable fluorochrome whose fluorescence amount is amplified by binding to a nucleic acid to a sample fluid containing the cells or microorganisms, allowing the mixture of the sample fluid and the fluorochrome to stand for a certain time, irradiating the cells or microorganisms with light having a specific wavelength without stirring the mixture, and detecting the fluorescence emitted from the cells or microorganisms.

The standing time after staining is preferably 30 minutes to 120 minutes.

To achieve the third object, the present invention is also adapted to add a membrane-permeable fluorochrome whose fluorescence amount is amplified by binding to a nucleic acid, a membrane-impermeable fluorochrome whose fluorescence amount is amplified by binding to a nucleic acid, and a fluorescence reagent for staining materials derived from animal cells or plant cells to a fluid obtained by homogenizing a food, wherein the membrane-impermeable fluorochrome whose fluorescence amount is amplified by binding to a nucleic acid and the fluorochrome for staining materials derived from animal cells or plant cells selected have a fluorescence spectrum peak at 550 nm or more and less than 680 nm, and adapted to count desired viable bacteria by adding these fluorochromes to the sample fluid to stain viable bacteria in the fluid, irradiating the viable bacteria with light having a specific wavelength, and detecting the fluorescence emitted from the viable bacteria.

(A) Invention Relating to First Object

Glycerin has a low environmental load since it has low bactericidal properties as used for frozen storage of bacteria and is excellent in biodegradability as used in foods and pharmaceuticals, and further less easily produces measurement disturbance due to generated foams since it also has low foaming properties. According to the present invention, the use of glycerin as a staining promoter for fluorochromes applied to cells or microorganisms (viable bacteria) in a microorganism test can reduce the problems of bactericidal and foaming properties and on biodegradability in conventionally used staining promoters (surfactants and chelating agents such as EDTA) to promote the fluorescence staining of cells or microorganisms, resulting in improving the accuracy of counting the cells or microorganisms.

(B) Invention Relating to Second Object

The use of plural types of membrane-permeable, nucleic acid-binding fluorochromes having different fluorescence spectra can detect a plurality of fluorescence spectra from desired cells or microorganisms (viable bacteria), thereby discriminate the desired cells or microorganisms from particles formed by the aggregation of the fluorochromes, based on the information of the types of the fluorescences detected, and thereby improve the accuracy of counting the cells or microorganisms.

A sample fluid can be allowed to stand after staining to secure the time for the fluorochrome to aggregate to reduce the number of the pigment particles in the sample fluid, resulting in improving the accuracy of counting cells or microorganisms.

(C) Invention Relating to Third Object

In detecting viable bacteria contained in a fluid obtained by homogenizing a food, fluorochromes having peaks of fluorescence spectra at 550 (inclusive) to 680 (exclusive) nm can be selected as a fluorochrome for killed bacteria and a fluorochrome for staining materials derived from animal cells or plant cells to separate and detect only the fluorescence of viable bacteria to be detected without separating the fluorescence to be excluded of killed cells, chloroplasts, mitochondria, and the like, thus enabling the simplification of an analytical circuit.

The present inventions relating to the first to third objects can singularly improve the accuracy of counting cells or microorganisms (viable bacteria); however, they further improve the accuracy of counting cells or microorganisms (viable bacteria) in combination.

This specification includes the contents as disclosed in the specification and/or drawings of Japanese Patent Application No. 2009-249647, which is a priority document of the present application.

BRIEF DESCRIPTION OF THE DRAWINGS

FIG. 2 (B) is a schematic diagram of a photomicrograph of the fluorescently-stained *Escherichia coli* according to the embodiment of the present invention.

FIG. 4 (B) is a diagram describing the appearance of light emission of a bacterial cell and pigment particles when stained by the two types of fluorochromes according to the embodiment of the present invention.

FIG. 5 is a drawing showing examples of light emission of the materials according to the embodiment of the present invention.

FIG. 8 (B) is a drawing showing other examples of fluorescence spectra of the four types of fluorochromes according to the embodiment of the present invention.

FIG. 9 is a drawing showing examples of light emission of the materials according to the embodiment of the present invention.

FIG. 11 (B) is a drawing showing an example of a decomposition structure including a passage for microorganism detection in a microorganism-detecting chip used in the microorganism-testing apparatus according to the embodiment of the present invention.

DESCRIPTION OF SYMBOLS

Figure 1:
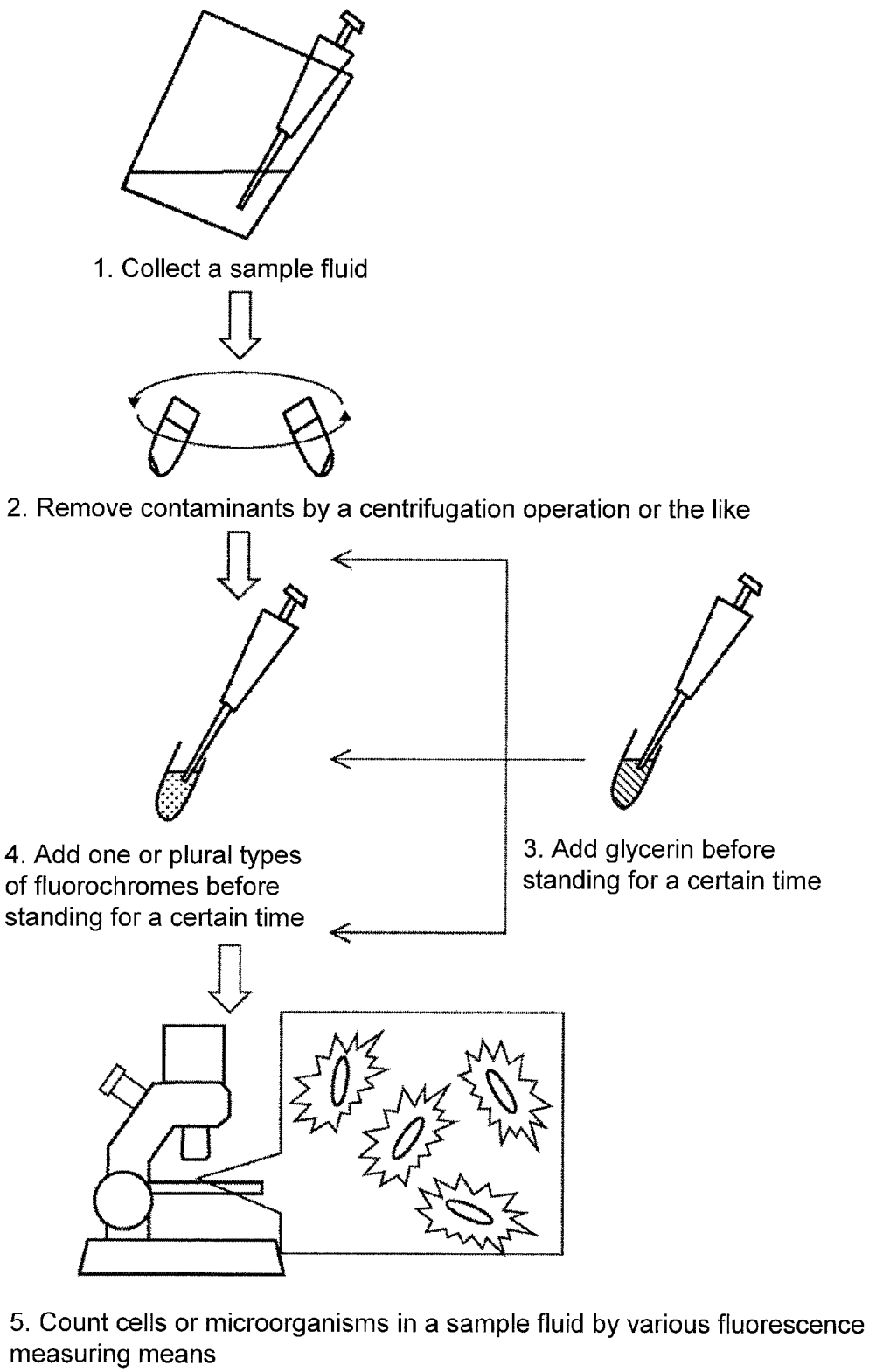
FIG. 1 is a diagram showing a staining protocol when the glycerin according to the embodiment of the present invention is used as a staining promoter.

1 Microorganism-Testing Apparatus
10 Microorganism-Testing Chip
11 Detector
14 Pressure-Supply Unit
17 Microorganism-Detecting Section
18 System Unit
19 Output Unit
111 Excitation Light Source
113 Excitation Light
114 Objective Lens
119 Pinhole
121 Fluorescence
124 Scattered Light
125 X-Y Movable Stage
151 Sample Vessel
152 Microorganism-Staining Solution Vessel
156 Detection Solution Discarding Vessel
161 Window Frame Area for Detection
173 Microorganism Detection Passage
1171 Band-Pass Filter for Blue Fluorescence
1172 Band-Pass Filter for Orange-Colored Fluorescence
1173 Band-Pass Filter for Red Fluorescence
1174 Band-Pass Filter for Near-Infrared Fluorescence
1181, 1182 Condensing Lens
1201 Photodetector for Blue Fluorescence
1202 Photodetector for Orange-Colored Fluorescence
1203 Photodetector for Red Fluorescence
1204 Photodetector for Near-Infrared Fluorescence
1571 to 1573 Solution Passage
1581 to 1583 Ventilation Passage
1591 to 1593 Vent

DETAILED DESCRIPTION OF THE PREFERRED EMBODIMENTS

Referring to the drawings, embodiments of the present invention will be described below. In this respect, the embodiments described later are only illustrative, and other aspects by combination of the embodiments and combination and substitution with a known or well-known technique are also possible.

(A) Increased Fluorescence Intensity of Bacteria Using Staining Promoter

FIG. 1 is a flowchart for describing the staining protocol according to the embodiment of the present invention. A protocol for counting viable bacteria contained in a sample fluid such as food and drinking water by a fluorescence method is shown as an example.

(1) A certain amount is taken out of a test sample such as a stomached solution of food and drinking water to make a sample fluid.

(2) Concomitants other than desired viable bacteria are contained in the sample fluid. Concomitants larger than viable bacteria (about 1 micron in diameter) are removed by a means such as a centrifugation method. Other means for removing the concomitants include a filtration method and a column method.

(3) Glycerin is added to the sample fluid, which is then allowed to stand for a certain time (for example, 1 minute to 30 minutes). The addition of glycerin is intended to promote stainability by establishing a state in which a fluorochrome readily permeates into a bacterial cell (the details are described later). Thus, standing for a certain time after addition of glycerin increases stainability; however, the glycerin effect of promoting staining with the fluorochrome is obtained even when glycerin is added simultaneously with the fluorochrome or after addition of the fluorochrome. Too high a final concentration of glycerin may lead to the loss of the bioactivity of viable bacteria; however, the results of our studies using a culture method have confirmed that a final concentration of glycerin of 30% or less does not affect the bioactivity of viable bacteria or cause viable bacteria to be stained by an orthochromatic dye for killed bacteria.

(4) A fluorochrome is added thereto, and the sample is allowed to stand for a certain time (30 minutes to 120 minutes). There are the following two reasons why the sample is allowed to stand for a certain time during staining. The first reason is that in the case of a membrane-permeable, nucleic acid-binding fluorochrome, a certain time is necessary for the fluorochrome to enter viable bacteria and bind to nucleic acids in the viable bacteria. The second reason is that most of the membrane-permeable, nucleic acid-binding fluorochromes tend to aggregate with time in an aqueous solution because of their hydrophobicity. The certain standing time can be secured to promote the aggregation of pigment particles to reduce the number of the pigment particles. To prevent the dissociation of the pigment particles due to the energy of stirring, stirring after standing is preferably not performed. Plural types of fluorochromes may be used to discriminate between pigment particles and viable bacteria although the details are described later. Securing the certain standing time during staining has the effects of promoting staining and decreasing pigment particles, irrespective of using glycerin.

(5) Fluorescently-stained viable bacteria are observed and counted by fluorescence observation under a microscope or by a fluorescent measurement means such as fluorescence cytometry (image cytometry (hereinafter referred to as ICM)) and flow cytometry (hereinafter referred to as FCM)).

Figure 2A:
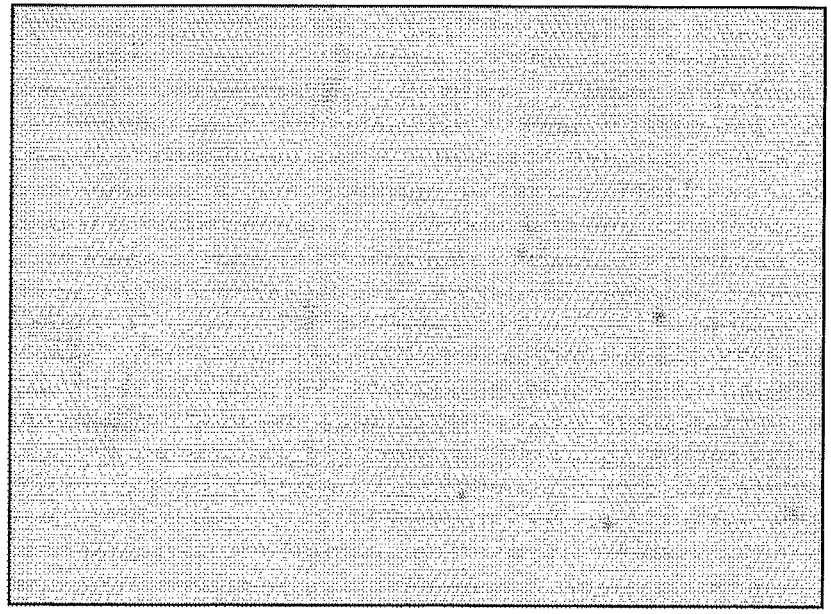
FIG. 2 (A) is a schematic diagram of a photomicrograph of *Escherichia coli* fluorescently-stained without using glycerin.
Figure 2B:
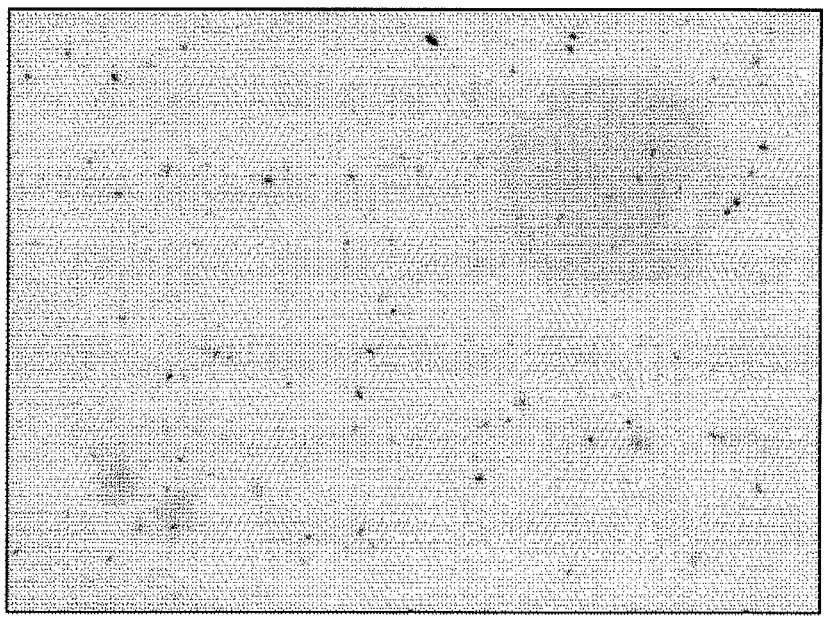

FIG. 2 schematically represents a microscopic image showing the effect of glycerin as a staining promoter (the actual microscopic image has a black background and a white bright point; however, in the schematic representation, the background is shown in white and the bright point, in black). The bright points in the schematic representation of the image represent bacteria (viable bacteria and killed bacteria) stained with a fluorochrome, and bacteria more stained by the fluorochrome form clearer images. FIG. 2 (A) is a schematic representation of a microscopic image when an orange-colored cyanine fluorochrome as a membrane-permeable, nucleic acid-binding fluorochrome is added to a fluid containing *Escherichia coli* (strain: NT9001, bacterial concentration: $10^8$ cells/ml) to a final concentration of 0.4 μM and the mixture was observed under a light microscope after standing at room temperature for 40 minutes. On the other hand, FIG. 2 (B) is a schematic representation of a microscopic image when glycerin and a cyanine orange-colored fluorochrome are added to a fluid containing *Escherichia coli* (strain: NT9001, bacterial concentration: $10^8$ cells/ml) to final concentrations of 10% and 0.4 μM, respectively and the mixture was observed under a light microscope after standing at room temperature for 40 minutes. Comparison of the schematic representations of two microscopic images shows that the addition of glycerin has promoted the stainability of bacteria with the fluorochrome since bacteria in the sample containing glycerin form clearer images. The present inventor expects the addition of glycerin to inhibit the function of membrane proteins of the bacteria to facilitate the permeation of the fluorochrome into the bacteria to promote stainability.

Figure 3:
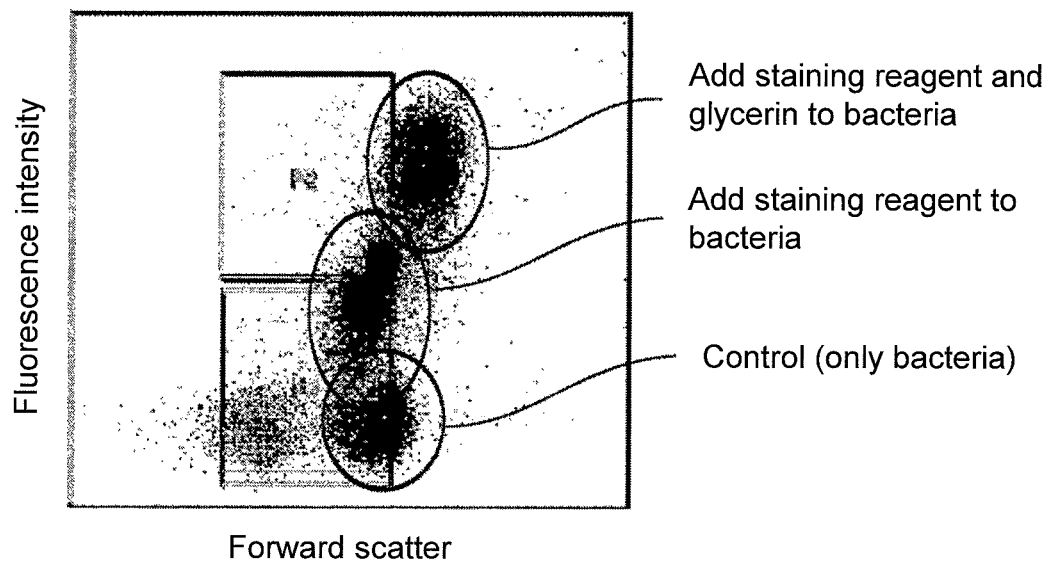
FIG. 3 is a drawing showing the measurements of the fluorescently-stained *Escherichia coli* according to the embodiment of the present invention using a fluorescence flow cytometer.

FIG. 3 reflects the effect of glycerin as a staining promoter, and shows the results of measuring the size and amount of fluorescence of *Escherichia coli* stained by a fluorochrome using a fluorescence flow cytometer. The horizontal axis represents the intensity of forward-scattered light, which indicates the size of particles, and the vertical axis represents the fluorescence amount. The samples measured are divided into three groups of the following conditions: (1) control (no fluorochrome or glycerin is added), (2) addition of a fluorochrome, and (3) addition of the fluorochrome and glycerin. The procedure of measurement will be described below.

(1) As control, a sample containing *Escherichia coli* (strain: NT9001, bacterial concentration: $10^5$ cells/ml) was measured without adding glycerin or the fluorochrome using a flow cytometer.

(2) A blue cyanine fluorochrome as a membrane-permeable, nucleic acid-binding fluorochrome was added to a sample containing *Escherichia coli* (strain: NT9001, bacterial concentration: $10^5$ cells/ml) to a final concentration of 0.8 μM, which was then measured using a flow cytometer after standing at room temperature for 40 minutes.

(3) Glycerin and a blue cyanine fluorochrome were added to a sample containing *Escherichia coli* (strain: NT9001, bacterial concentration: $10^5$ cells/ml) to final concentrations of 10% and 0.8 μM, respectively, which was then measured using a flow cytometer after standing at room temperature for 40 minutes.

FIG. 3 shows that the addition of glycerin promoted the stainability of viable and killed bacteria (hereinafter referred to as "V/K bacteria") with the fluorochrome since the fluorescence of bacteria in the sample containing glycerin was more intense.

Glycerin has a low environmental load since it has low bactericidal properties as used for frozen storage of bacteria and is excellent in biodegradability as used in foods and pharmaceuticals, and further less easily produces measurement disturbance due to generated foams since it also has low foaming properties. From these points, it can be said to be superior as a staining promoter to conventionally known surfactants and EDTA.

(B) Removal of Influence of Pigment Particles Using Double Staining

Figure 4A:
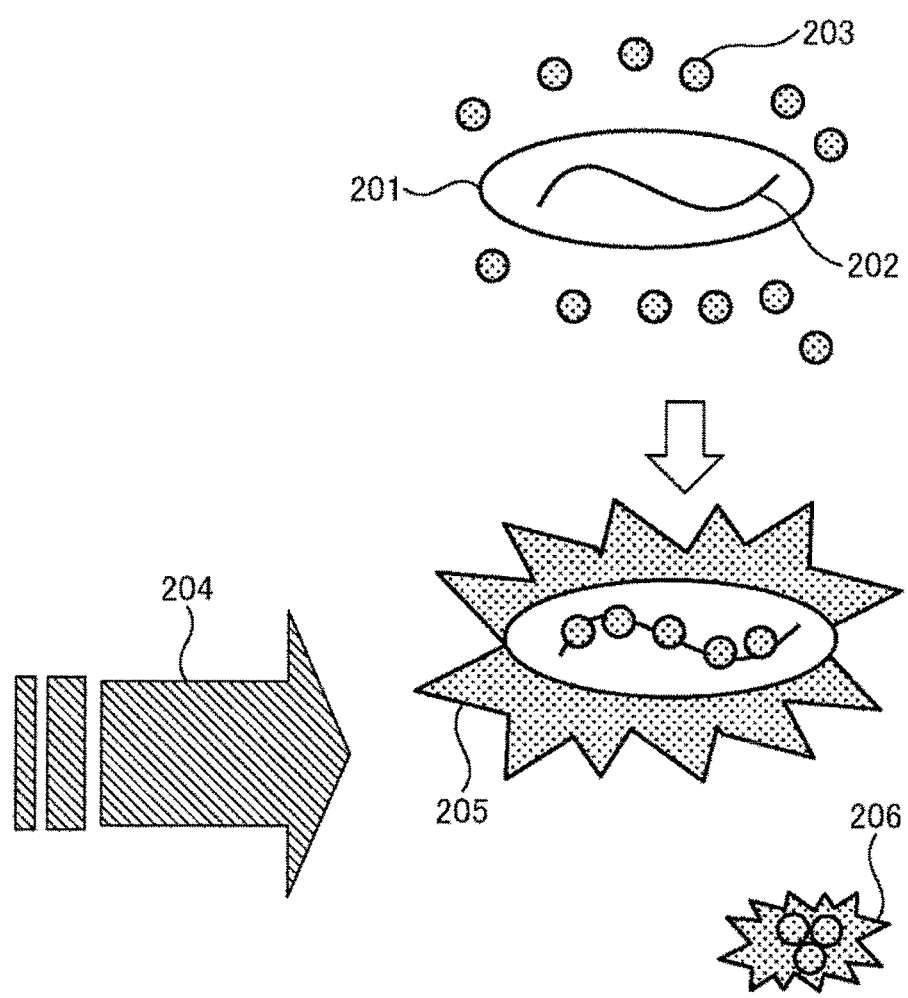
FIG. 4 (A) is a diagram describing the appearance of light emission of a bacterial cell and pigment particles when stained by one type of a fluorochrome.
Figure 4B:
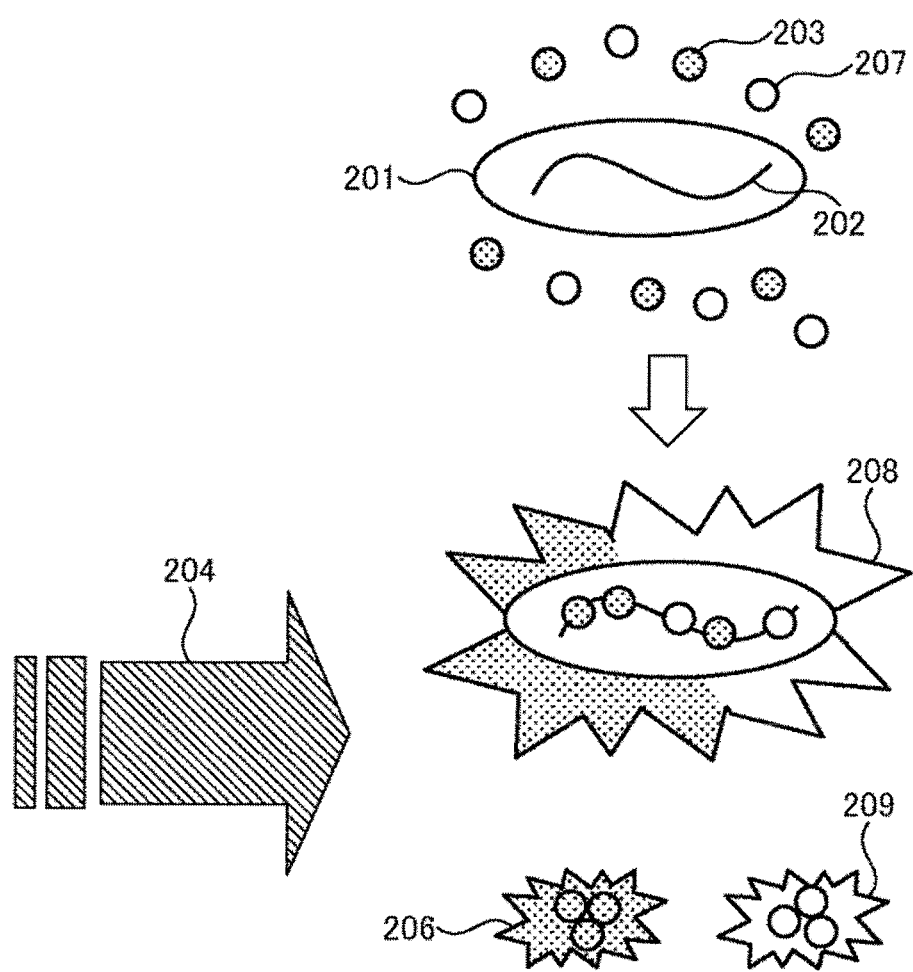

FIGS. 4 (A) and 4 (B) are illustrative pictures depicting the principle of discrimination between viable bacteria and pigment particles of a fluorochrome using double staining.

FIG. 4 (A) shows the appearance of fluorescences emitted by a viable bacterium 201 and an aggregate of molecules 203 of a first fluorochrome which is membrane-permeable and whose fluorescence amount is amplified by binding to nucleic acid when the viable bacterium was stained with the first fluorochrome. When a fluid containing the viable bacterium is mixed with the first fluorochrome, because the molecule 203 of the first fluorochrome is membrane-permeable, some of the molecules 203 of the first fluorochrome permeate the cell membrane of the viable bacterium 201 and binds to DNA 202 of the viable bacterium 201. Some of the molecules 203 of the first fluorochrome not binding to the DNA aggregate and form particles. When irradiated with excitation light 204, which excites the first fluorochrome, in this state, the viable bacterium 201 emits fluorescence 205 of the first fluorochrome and the aggregate of the molecules 203 of the first fluorochrome also emits fluorescence 206. Because both of the fluorescence 205 and the fluorescence 206 are the fluorescence of the first fluorochrome, the viable bacterium 201 and the particles of the molecules 203 of the first fluorochrome cannot be distinguished based only on the information of wavelength. If there were a great difference in the intensity of fluorescence therebetween, the two could be discriminated from each other based on the intensity difference; however, the fluorescence intensity distribution of the viable bacterium often overlaps with the fluorescence intensity distribution of the pigment particles, making it difficult to discriminate between the viable bacterium 201 and the aggregate of the molecules 203 of the first fluorochrome.

FIG. 4 (B) shows the appearance of fluorescences emitted by a viable bacterium 201 and aggregates of molecules 203 and 207 of two types of fluorochromes (a first fluorochrome and a second fluorochrome, respectively) which are membrane-permeable and whose fluorescence amount is amplified by binding to nucleic acid when the viable bacterium is stained by the two types of fluorochromes. When a fluid containing the viable bacterium is mixed with the first fluorochrome and the second fluorochrome, because the molecule 203 of the first fluorochrome and the molecule 207 of the second fluorochrome are membrane-permeable, some of the molecules 203 of the first fluorochrome and some of the molecules 207 of the second fluorochrome permeate the cell membrane of a viable bacterium 201 and binds to DNA 202 of the viable bacterium 201. Some of the molecules 203 of the first fluorochrome and some of the molecules 207 of the second fluorochrome not binding to the DNA aggregate and form particles. When irradiated with excitation light 204, which excites the first fluorochrome and the second fluorochrome, in this state, the viable bacterium 201 emits fluorescence 208, the aggregate of the molecules 203 of the first fluorochrome emits fluorescence 206, and the aggregate of the molecules 207 of the second fluorochrome emits fluorescence 209. The fluorescence 208 is fluorescence in which the fluorescences of the first fluorochrome and the second fluorochrome are combined; however, the viable bacterium 201 can be distinguished from the aggregate of the molecules 203 of the first fluorochrome and the aggregate of the molecules 207 of the second fluorochrome, based only on the information of wavelength because the fluorescence 206 is fluorescence of the first fluorochrome and the fluorescence 209 is fluorescence of the second fluorochrome.

FIG. 5 shows the types of fluorescences emitted from V/K bacteria (viable bacteria and killed bacteria) and particles of the first and second fluorochromes when V/K bacteria were stained with two types of fluorochromes by this method. V/K bacteria emit the fluorescences of the two types of fluorochromes because they are stained with the first fluorochrome and the second fluorochrome; however, the particles of the first fluorochrome emit only the fluorescence of the first fluorochrome and the particles of the second fluorochrome emit only the fluorescence of the second fluorochrome.

This method enables the discrimination between desired particles of V/K bacteria or the like and pigment particles based only on the information of wavelength, and therefore is a method useful for fluorescence cytometry (ICM, FCM) in which desired particles is counted from the information of fluorescence. The method is highly effective particularly when concomitants cannot be removed before counting by purification such as by centrifugation as in a fluorescence flow cytometry method using a microorganism-testing chip described later. This facilitates the exclusion of pigment particles which have been a factor for misdetection, and thus can improve the counting accuracy and the lower counting limit.

Figure 6:
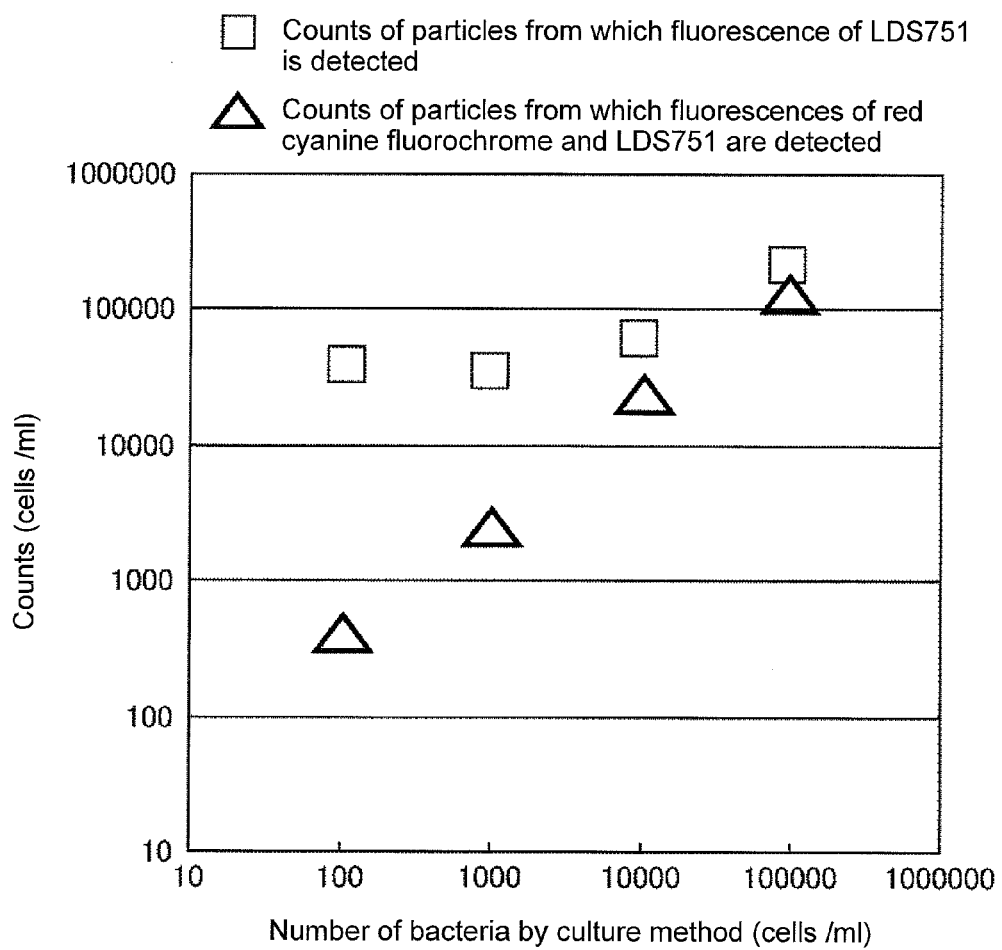
FIG. 6 is a drawing describing the relationship of counts on a flow cytometer when staining was performed with the two types fluorochromes according to the embodiment of the present invention to the number of bacteria obtained by a culture method.

FIG. 6 is a drawing showing the results of demonstrating the effect of removing the influence of pigment particles by double staining using a flow cytometer. LDS751 (final concentration: 1 µg/ml) and a red cyanine fluorochrome (final concentration: 0.4 µM), which are membrane-permeable and nucleic acid-binding fluorochromes, are added to a fluid containing *Escherichia coli* (strain: NT9001, final bacterial concentration: $10^2$ to $10^5$ cells/ml), followed by measuring the number of the stained bacteria using a flow cytometer to compare the measured number with the number of bacteria obtained by a culture method. FIG. 6 describes (1) the count of particles on which the fluorescence of LDS751 was detected when the number of bacteria in the fluid was changed and (2) the count of particles on which LDS751 and the red cyanine fluorochrome were simultaneously detected. Particularly, LDS751 is a fluorochrome having numerous pigment particles and contains about $10^4$ to $10^5$/ml of pigment particles. Thus, when the bacterial concentration is overwhelmingly lower than that of pigment particles of LDS751, it is difficult to accurately determine the number of bacteria only from the fluorescence of LDS751. If the upper limit of the number of pigment particles contained in the sample is the lower limit of the number of bacteria, the lower limit of the number of the bacteria when only LDS751 is used is $10^5$ cells/ml. In contrast, when both of LDS751 and the red cyanine fluorochrome are used, the number of bacteria can be counted with high accuracy because particles from which the fluorescences of both fluorochromes are simultaneously detected are detected as bacteria and the influence of pigment particles of LDS751 and the red cyanine fluorochrome is removed. It has been demonstrated that the simultaneous staining can decrease the lower detection limit for the number of bacteria to $10^2$ cells/ml.

Because a bacterial cell can be stained by a plurality of fluorochromes, the use of more types of fluorochromes improves the separation rate between pigment particles and bacteria. However, because the fluorescence of a fluorochrome has a spectrum, the peaks of fluorescence spectra are preferably a minimum of 50 nm away from each other to accurately separate the fluorescences thereof.

The addition of glycerin as a staining promoter in staining bacteria can increase the number of pigment particles several times as compared to no addition of glycerin. However, pigment particles can be excluded from the counting target by double staining to accurately count bacteria even when the number of pigment particles is increased, which can improve detection accuracy in combination with the glycerin effect of increasing fluorescence intensity.

According to the present embodiment, two types of pigments for V/K bacteria were used to count V/K bacteria; however, two types of pigments for killed bacteria can be used to count killed bacteria in a sample fluid with high accuracy. Because the number of killed bacteria cannot be counted by a culture method, this method provides a means very useful for the counting of killed bacteria.

(C) Setting of Wavelength Region in Multi-Staining

Figure 7:
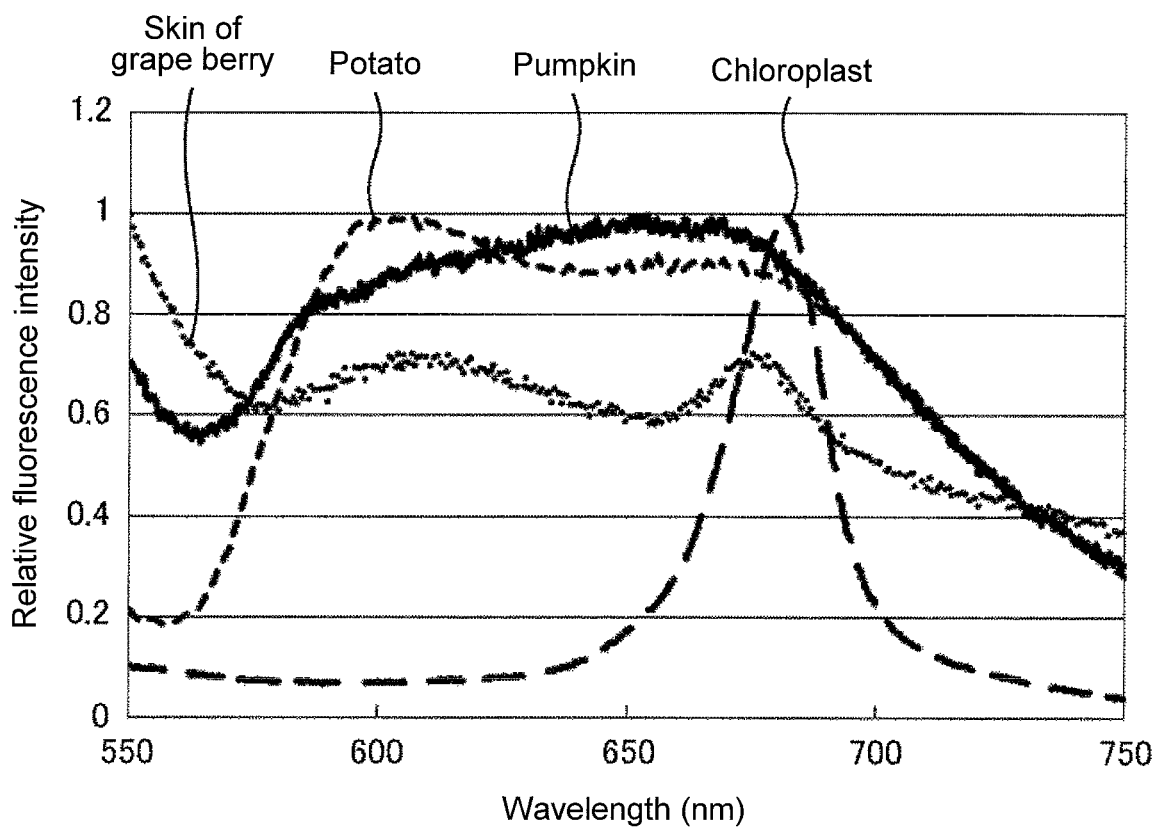
FIG. 7 is a drawing showing spectra of autofluorescences of four types of vegetables.

FIG. 7 is a drawing showing fluorescence spectra when vegetables containing chloroplasts and chromatophores emitting autofluorescences were excited with an excitation light having a wavelength of 532 nm. Spinach holds many chloroplasts containing chlorophyll as a green pigment; potato holds amyloplasts storing starch; pumpkin holds many chromatophores containing carotenoids as yellow pigments; and the skin of grape berry holds many chromatophores containing anthocyanin as a purple pigment. These vegetables emit fluorescence in the yellow to red wavelength region (550 nm or more and less than 680 nm). Thus, when bacteria in a food are detected by fluorescence cytometry (ICM, FCM), a pigment for staining V/K bacteria (viable bacteria and killed bacteria) is preferably selected from pigments emitting fluorescence in the blue or near-infrared wavelength region, which includes no wavelength region of 550 nm to 680 nm, to avoid a reduction in detection accuracy due to particles emitting these autofluorescences. It is no problem that the wavelength region for pigments for staining targets such as mitochondria to be excluded from counting is within the range of 550 nm or more and less than 680 nm. It is also no problem that the wavelength region for pigments for staining only killed bacteria is within the range of 550 nm or more and less than 680 nm.

Figure 8A:
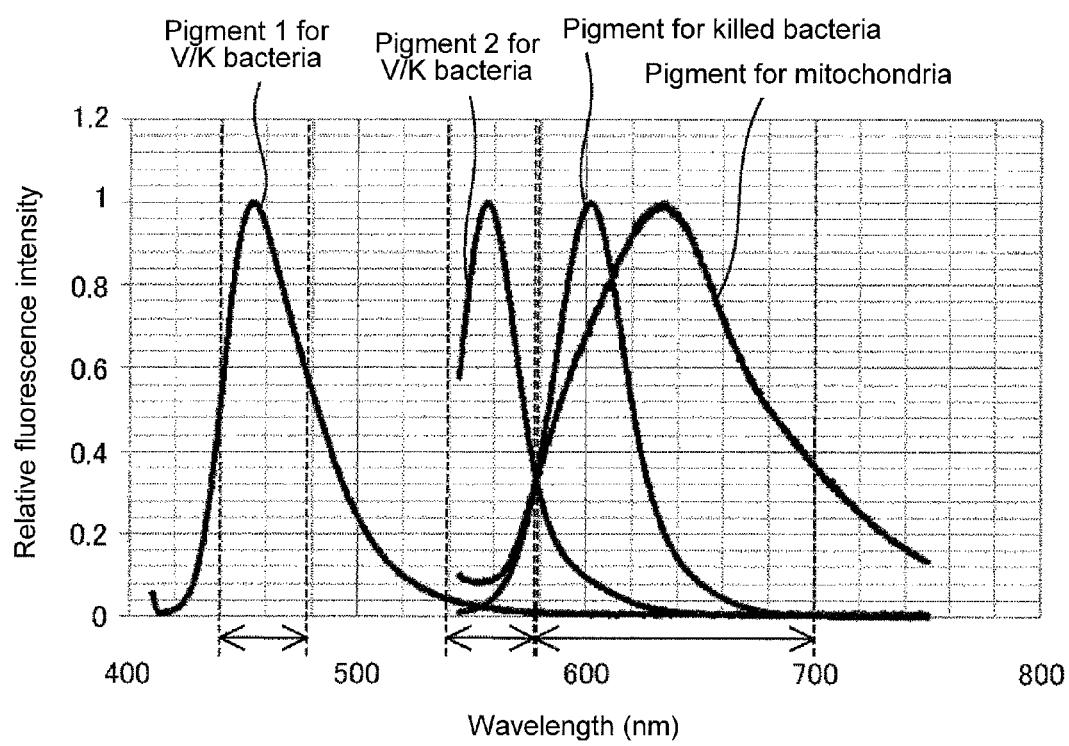
FIG. 8 (A) is a drawing showing fluorescence spectra of the four types of fluorochromes according to the embodiment of the present invention.
Figure 8B:
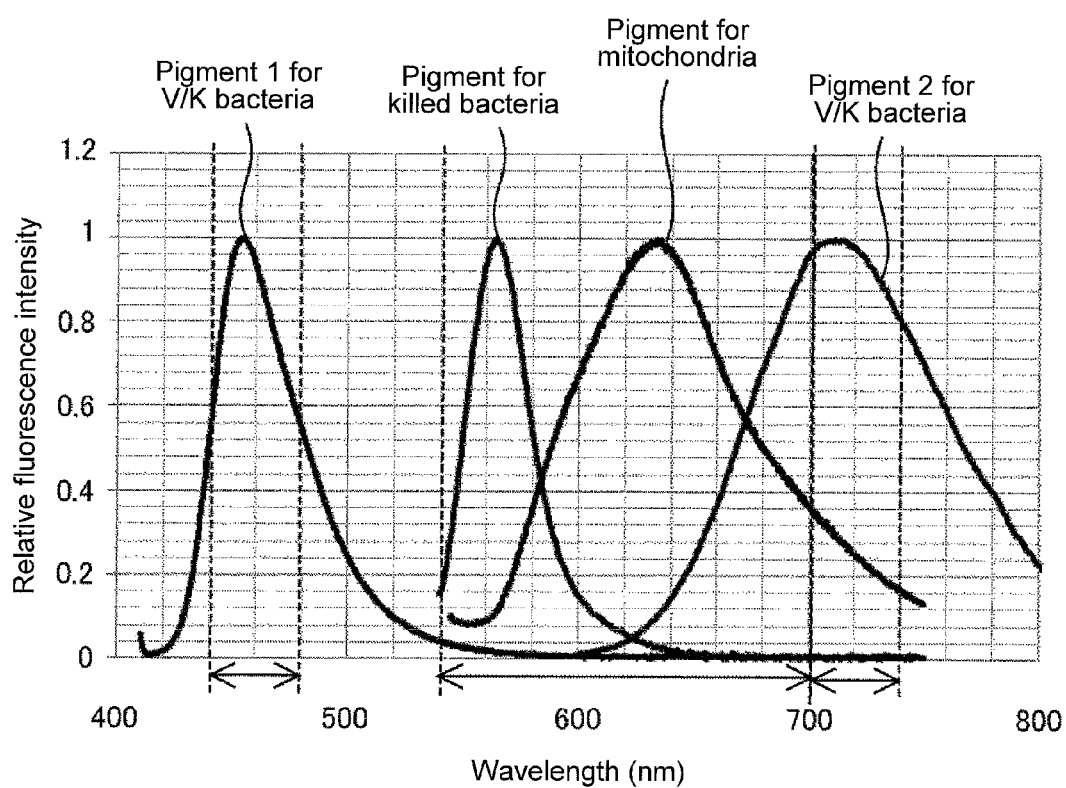

FIGS. 8 (A) and 8 (B) show examples of the wavelength region for fluorochromes used for counting viable bacteria using a fluorescence cytometer. According to the present embodiment, an orange-colored cyanine fluorochrome for killed bacteria (peak wavelength of fluorescence spectrum: 570 nm) which is a membrane-impermeable, nucleic acid-binding fluorochrome is selected as a fluorochrome for staining killed bacteria to be excluded from counting; a red fluorochrome for mitochondria (peak wavelength of fluorescence spectrum: 640 nm), as a red fluorochrome for staining mitochondria to be similarly excluded from counting; a blue cyanine fluorochrome for V/K bacteria (peak wavelength of fluorescence spectrum: 450 nm) as a membrane-permeable, nucleic acid-binding fluorochrome and an orange-colored cyanine fluorochrome (peak wavelength of fluorescence spectrum: 550 nm) as a membrane-permeable, nucleic acid-binding fluorochrome (FIG. 8 (A)), or a blue cyanine fluorochrome for V/K bacteria (peak wavelength of fluorescence spectrum: 450 nm) and LDS751 (peak wavelength of fluorescence spectrum: 720 nm) (FIG. 8 (B)), as a pigment for staining V/K bacteria (viable bacteria and killed bacteria). This method cannot distinguish among killed bacteria, mitochondria, and chromatophores and chloroplasts of vegetables; however, the overlap of fluorescence spectra therefrom is not a problem for the counting of viable bacteria because these materials are targets to be excluded from counting. Examples of other candidates for pigments for staining V/K bacteria (viable bacteria and killed bacteria) include DAPI (4', 6-diamidine-2'-phenylindole, peak wavelength of fluorescence spectrum: 460 nm), HOECHST33258 (peak wavelength of fluorescence spectrum: 460 nm), HOECHST34580 (peak wavelength of fluorescence spectrum: 500 nm), and a red cyanine fluorochrome for V/K bacteria (peak wavelength of fluorescence spectrum: around 670 nm). Examples of other candidates for pigments for staining killed bacteria include PI (propidium iodide, peak wavelength of fluorescence spectrum: 630 nm) and EB (ethidium iodide, peak wavelength of fluorescence spectrum: 605 nm). Examples of other candidates for pigments for staining mitochondria include an orange-colored fluorochrome for mitochondria (peak wavelength of fluorescence spectrum: 576 nm).

The wavelength region of fluorescence to be excluded from counting is defined as 550 nm or more and less than 680 nm with the wavelength region of that of a pigment for staining V/K bacteria (viable bacteria and killed bacteria) defined as the other wavelength region and concentration is made on the determination of whether the fluorescence is that from viable bacteria or the other materials, thereby enabling the analytical circuit of a fluorescence cytometer to be simplified and also enabling production cost to be greatly reduced because it is no problem to collectively detect lights having the wavelengths to be excluded (550 nm or more and less than 680 nm) using one to two detectors.

FIG. 9 shows the types of fluorescences from viable bacteria, killed bacteria, food-derived materials (mitochondria, chloroplasts, chromatophores, starch, glycogen, and cellulose), and particles of pigments when in a food-derived sample, a blue cyanine fluorochrome (blue fluorescence) and LDS751 (near-infrared fluorescence) for V/K bacteria are used as fluorochromes for staining V/K bacteria; an orange-colored fluorochrome (orange-colored fluorescence) for killed bacteria, as a fluorochrome for staining only killed bacteria; and a red fluorochrome (red fluorescence) for mitochondria, as a fluorochrome for staining mitochondria. When a food-derived sample is measured using a fluorescence cytometer, particles can be identified as follows, base on FIG. 9.

(1) Viable bacteria emit blue and near-infrared fluorescences because they are stained by only the fluorochromes for staining V/K bacteria.

(2) Killed bacteria emit blue, orange and near-infrared fluorescences because they are also stained by the fluorochrome for staining only killed bacteria.

(3) Chloroplasts and chromatophores have DNA in their inside; however, when they are stained with the fluorochromes for staining V/K bacteria, their fluorescences are weak because the DNA has a short length of 150 kbp as compared to DNA (several Mbp) in bacteria. These materials emit orange or red autofluorescence, enabling them to be distinguished from viable bacteria.

(4) Mitochondria are present in two types: those derived from animal cells and plant cells. DNA in animal cell mitochondria have a very short length of 10 kbp, while DNA in plant cell mitochondria are also reported to have a length approaching that in bacteria. Thus, when stained with a fluorochrome for staining V/K bacteria, mitochondria are also present which emit fluorescence similar to that from bacteria. However, mitochondria can be distinguished from viable bacteria because they are stained by a fluorochrome for mitochondria and thereby emit red fluorescence.

(5) Materials such as starch, glycogen, and cellulose have no nucleic acid; however, they emit fluorescences of various fluorochromes by the non-specific adsorption of the fluorochromes thereto.

In accordance with the above, materials other than viable bacteria can be distinguished from the viable bacteria because such materials emit orange or red fluorescence.

(6) Particles of each fluorochrome emit only one type of fluorescence because they emit only the fluorescence of a fluorochrome forming them. Thus, they can be distinguished from viable bacteria.

As described above, according to the present embodiment, only the fluorescence of viable bacteria to be detected can be separated and detected without separating the fluorescences to be excluded of killed cells, chloroplasts, mitochondria, and the like, thus enabling the simplification of an analytical circuit.

(D) Example of Overall Configuration of Microorganism-Testing Apparatus

Figure 10:
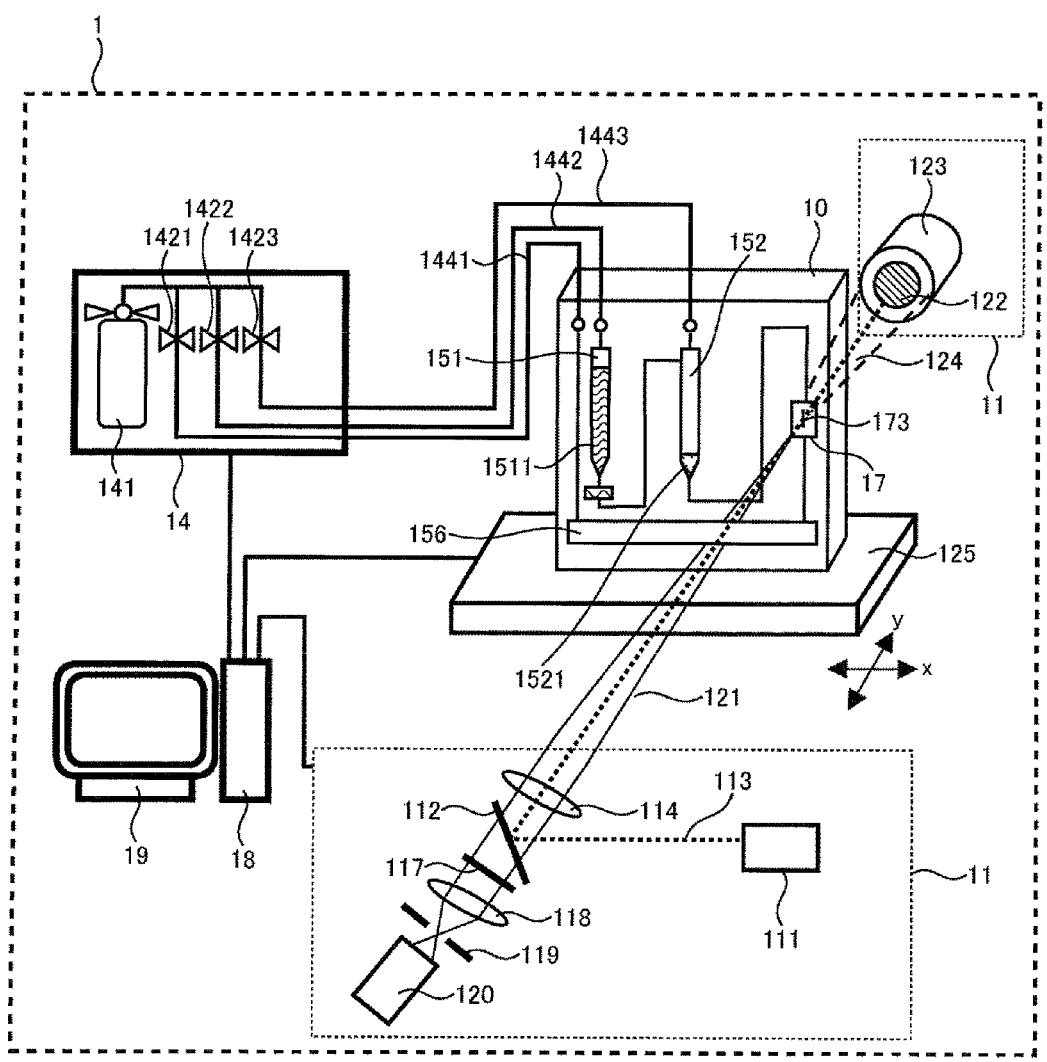
FIG. 10 is a drawing showing a skeleton framework of the microorganism-testing apparatus according to the embodiment of the present invention.

FIG. 10 shows the configuration diagram of a microorganism-testing apparatus 1 according to the embodiment of the present invention. The microorganism-testing apparatus 1 comprises a microorganism-testing chip 10 holding a sample and a reagent in its inside and having a mechanism for performing a step necessary for counting microorganims in the inside, a pressure-supply unit 14 for supplying high-pressure gas into the microorganism-testing chip 10 via connecting pipes 1441 to 1443 connected to the microorganism-testing chip 10 and controlling the conveyance of the sample and the reagent in the microorganism-testing chip 10 to perform the step necessary for counting microorganims, an X-Y movable stage 125 for holding the microorganism-testing chip 10 and adjusting the position of the microorganism-testing chip 10, and a detector 11 for irradiating excitation light on the microorganims in the microorganism-testing chip 10 and converting scattered light and fluorescence from microorganisms into electrical signals. A system unit 18 connected to the microorganism-testing apparatus 1 performs the outputting of a control signal to the pressure-supply unit 14 and the processing of the electrical signals inputted from the detector 11. The counting results obtained by the processing of electrical signals are displayed on an output unit 19 connected to the system unit 18.

The pressure-supply unit 14 has a cylinder 141 with a pressure regulator. An air, an inert gas, or the like at high pressure is enclosed in the cylinder 141. The cylinder 141 and vents 1591 to 1593 (FIG. 13) in the microorganism-testing chip 10 are connected by chip connecting pipes 1441 to 1443. The chip connecting pipes 1441 to 1443 are provided with valves 1421 to 1423, respectively. The valves 1421 to 1423 are opened or closed to supply gas at predetermined pressure to vessels in the microorganism-testing chip 10 or open the vessels in the microorganism-testing chip 10 to the atmosphere. The conveyance of the sample and the reagent in the microorganism-testing chip 10 is achieved by this control of pressure. Such a microorganism-testing apparatus is described in detail in JP Patent Publication (Kokai) Nos. 2008-157829 A and 2009-178078 A as filed earlier by the present inventors, and the like.

Figure 13:
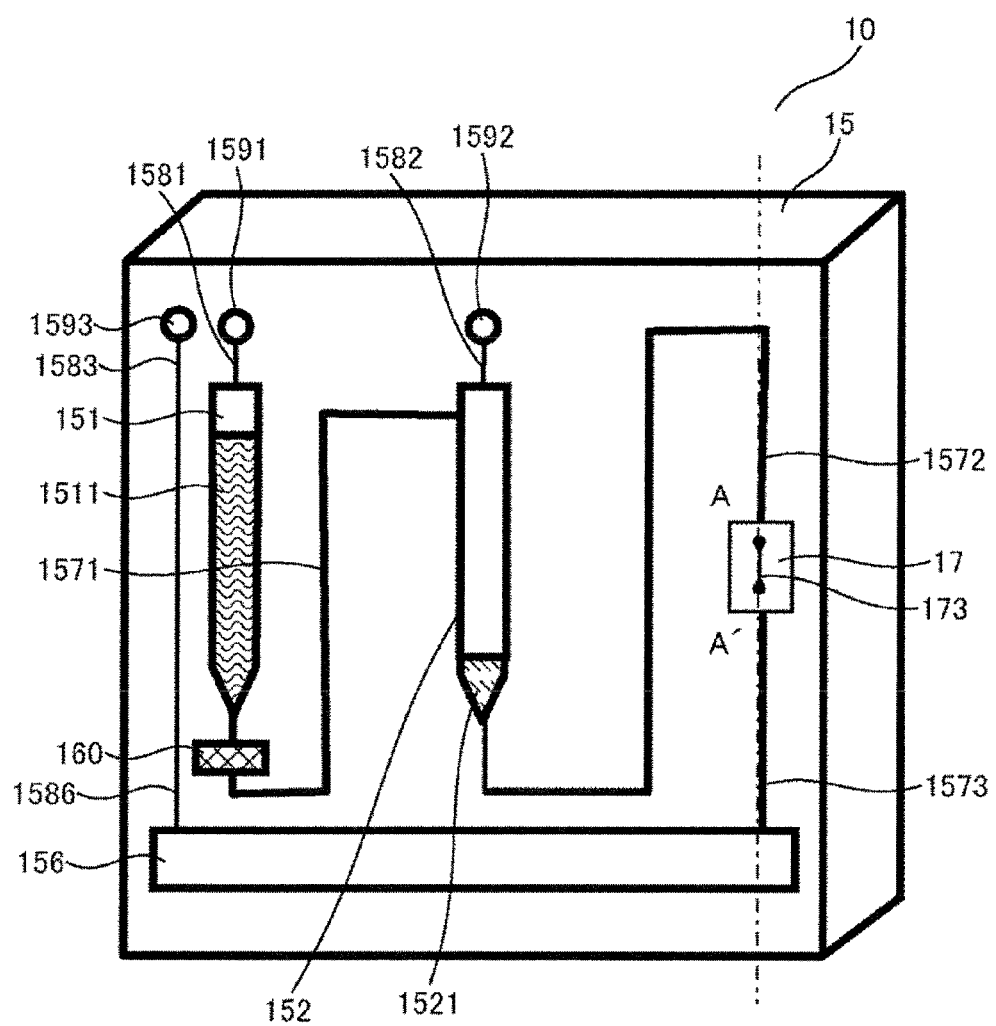
FIG. 13 is a drawing showing a skeleton framework of a microorganism-testing chip used in the microorganism-testing apparatus according to the embodiment of the present invention.

As shown in FIGS. 10 and 13, the microorganism-testing chip 10 comprises a sample vessel 151 for holding a sample 1511, a microorganism-staining solution vessel (reactor) 152 for holding a staining solution (reagent solution) 1521 for staining microorganisms in the sample and mixing and reacting the sample with the staining solution, a microorganism-detecting section 17 being irradiated with excitation light 113 from a excitation light source 111 and having a microorganism detection passage 173 for observing the microorganism in its inside, a detection solution discarding vessel 156 for discarding a mixture of the sample 1511 and the staining solution 1521 having passed through the microorganism detection passage 173, solution passages 1571 to 1573 (FIG. 13) for providing connections among the sample vessel 151, the microorganism-staining solution vessel 152, and the microorganism detection passage 173 and flowing the sample 1511 and the mixture, and ventilation passages 1581 to 1582 (FIG. 13) for connecting the vessels to vents 1591 to 1592 (FIG. 13) through which a high-pressure gas for allowing the sample 1511 and the mixture to flow is supplied from the pressure-supply unit 14. In the present specification, the sample vessel 151 side along the flow of the sample fluid is defined as the upstream side and the microorganism detection passage 173 side, as the downstream side.

When the step of adding glycerin to a sample fluid before or after or simultaneously with the mixing of the sample fluid and a fluorochrome is provided, a vessel for holding glycerin is set, for example, downstream of the microorganism-staining solution vessel 152 (the diagrammatic representation is abbreviated).

The outline of the detector 11 will be described based on FIG. 10. The detector 11 comprises the excitation light source 111, a scattered light-detecting section, and a fluorescence-detecting section. Of these, the scattered light-detecting section comprises a scattered light detector 123 for detecting scattered light 124 from a microorganism flowing through the microorganism detection passage 173 and a baffle 122 for preventing the excitation light 113 from the excitation light source 111 from directly entering the scattered light detector 123. On the other hand, the fluorescence-detecting section comprises an objective lens 114 for condensing fluorescence 121 from microorganisms passing through the microorganism detection passage 173 to make parallel light, a dichroic mirror 112 reflecting the excitation light 113 in the direction of the microorganism-detecting section 17 while passing the fluorescence 121, a band-pass filter 117 passing the fluorescence 121, a condensing lens 118 for condensing parallel light, a pinhole 119 used as a space filter for cutting stray light, and a photodetector 120 for detecting light passing through the band-pass filter 117. The irradiation section and the detecting section are arranged so that their foci overlap one another and configured so that at measurement, the microorganism detection passage 173 can be adjusted to the position of the focus.

The detector 11 irradiates the microorganism detection passage 173 with the excitation light 113 outputted from the excitation light source 111 and detects the amount of scattered light generated from the microorganism detection passage 173 and the amount of fluorescence generated from the microorganism-detecting section 17 to obtain the relationship of each amount to the movable position of the X-Y movable stage 125 as a profile. The detector 11 also movably controls the X-Y movable stage 125 based on the obtained profile to adjust the microorganism-testing chip 10 (specifically, the microorganism detection passage 173) to a position suitable for detection.

(E) Example of Structure of Microorganism-Testing Chip

Figure 11A:
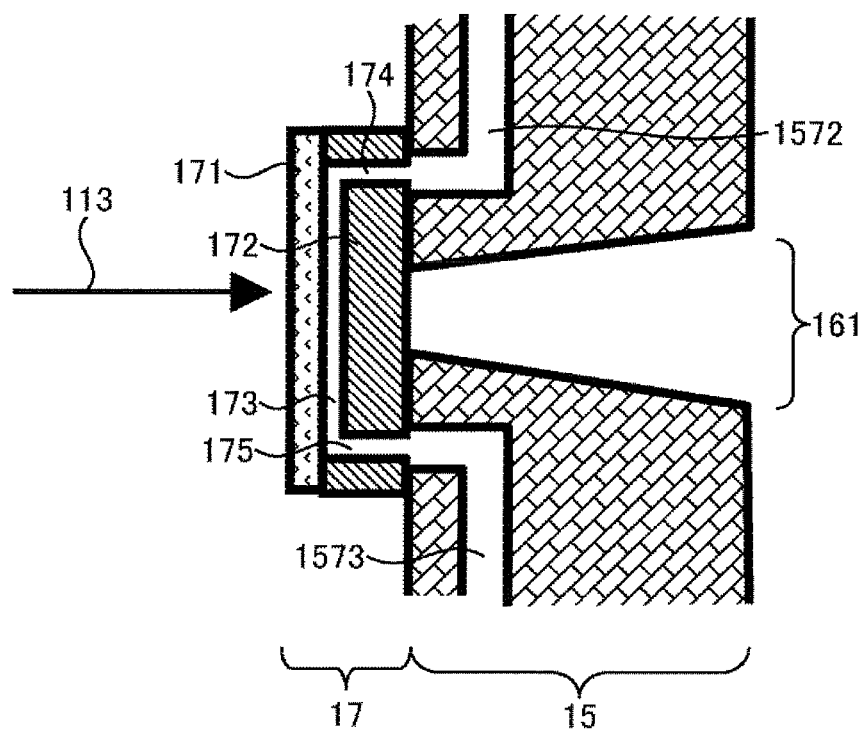
FIG. 11 (A) is a drawing showing an example of a section including a passage for microorganism detection in a microorganism-detecting chip used in the microorganism-testing apparatus according to the embodiment of the present invention.
Figure 11B:
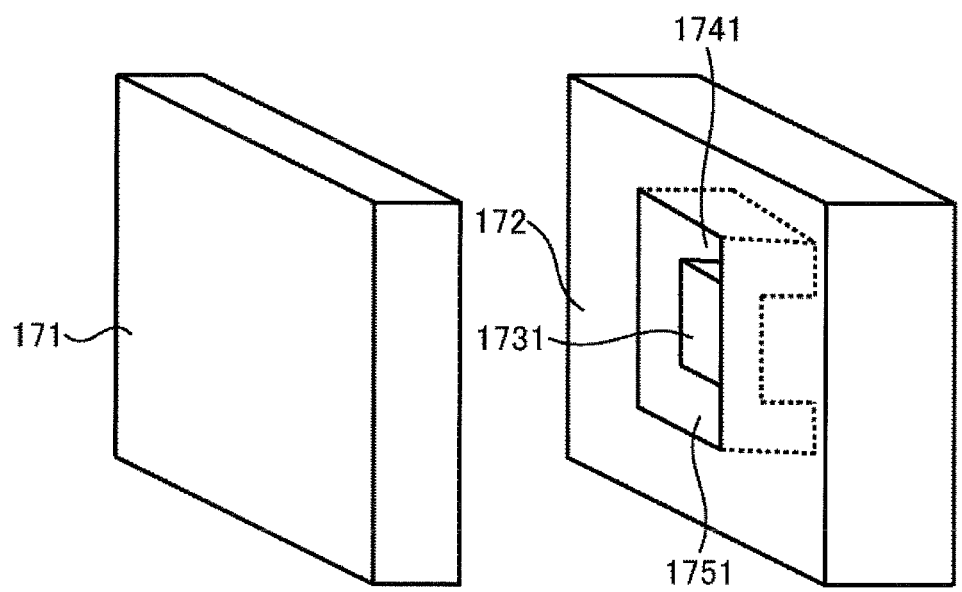

The structure of the microorganism-detecting section 17 in the microorganism-testing chip 10 will be described using FIGS. 11 (A) and 11 (B). FIG. 11 (A) shows a sectional drawing of the joint between a main body 15 of the microorganism-testing chip 10 and the microorganism-detecting section 17. The main body 15 and the microorganism-detecting section 17 have been produced in separate steps. FIG. 11 (B) shows an exploded perspective view of the microorganism-detecting section 17.

First, a method for producing the microorganism-detecting section 17 will be described. The microorganism-detecting section 17 comprises a cover member 171 and a passage member 172 and both consist of thin flat plates. The passage member 172 has a groove 1731 formed thereon, and the groove 1731 has through-bores 1741 and 1751 formed at the ends. The cover member 171 and the passage member 172 are glued together so that the side on which the groove 1731 is formed provides the side to be glued. This lamination forms the microorganism-detecting section 17. The groove 1731 of the passage member 172 and the cover member 171 constitute the microorganism detection passage 173. The through-bores 1741 and 1751 of the passage member 172 form a microorganism detection passage inlet 174 and a microorganism detection passage outlet 175.

A solution passage 1572 between the microorganism-staining solution vessel and the microorganism detection passage formed in the main body 15 changes the direction of the passage at its lower end and forms an opening on the surface of the main body 15. Similarly, a solution passage 1573 between the microorganism detection passage and the detection solution discarding vessel changes the direction of the passage at its upper end and forms an opening on the surface of the main body 15. The opening of the solution passage 1572 is connected to the microorganism detection passage inlet 174, and the opening of the solution passage 1573 is connected to the microorganism detection passage outlet 175.

The main body 15 has a window frame area for detection 161 formed. The window frame area for detection 161 is a through-bore or a through-groove. The window frame area for detection 161 is formed between the opening of the solution passage 1572 and the opening of solution passage 1573. The fabricated microorganism-detecting section 17 is connected and attached to the main body 15 as described above. As shown in FIG. 11 (A), the microorganism-detecting section 17 is attached so that the microorganism detection passage 173 is disposed over the window frame area for detection 161 of the main body 15.

In the present embodiment, the window frame area for detection 161 that is the through-bore or through-groove of the main body 15 is provided behind the microorganism detection passage 173. Thus, the excitation light 113 irradiates only the microorganism-detecting section 17 and does not irradiates the main body 15. Consequently, reflected light or autofluorescence from the main body 15 causing an increase in background light does not occurs. For the excitation light 113 having passed through the microorganism detection passage 173 not to be irradiated on the main body 15, the section of the through-bore forming the window frame area for detection 161 preferably increases along the radiation of the excitation light 113.

The thickness of the cover member 171 is set, for example, to 0.01 μm to 1 mm. The thickness of the passage member 172 is set, for example, to 0.01 μm to 1 mm. The cross-sectional shape of the microorganism detection passage 173 is formed, for example, into a square, rectangle or trapezoid shape. A larger section size of the microorganism detection passage 173 makes pressure loss lower; however, to flow one microorganism cell at a time, it is desirable that the size is small. The one side of the section of the microorganism detection passage 173 is preferably, for example, 1 μm to 1 mm, and its length is preferably, for example, 0.01 mm to 10 mm. The optical axis of the excitation light 113 irradiated on the microorganism detection passage 173 is normal to the direction vector of the microorganism detection passage 173.

The microorganism-testing chip 10 is constituted by inexpensive materials since it is of a disposal type, and also composed of materials having a low autofluorescence and excellent in optical transparency, profile irregularity, a refractive index, and the like to make it suitable for measuring fluorescence. For example, the cover member 171 is constituted by glass, quartz, or the like, and the passage member 172 is composed of polymethyl methacrylate, polydimethylsiloxane, cyclo-olefin polymer, polyethylene terephthalate, polycarbonate, or the like in consideration of microprocessing. When the passage member 172 is composed of polydimethylsiloxane, the joining between the cover member 171 and the passage member 172 utilizes the self-adhesiveness of polydimethylsiloxane. The cover member 171 and the passage member 172 may also be produced using cyclo-olefin polymer, polymethyl methacrylate, polyethylene terephthalate, or polycarbonate. This increases the amount of autofluorescence per unit volume by a factor of about 3 or more compared to when the cover member 171 is produced using glass or quartz and the passage member 172 is produced using polydimethylsiloxane; thus, the cover member 171 and the passage member 172 preferably have a thickness of 0.01 mm to 0.3 mm (both inclusive). The main body 15 is formed using a material which is easy to microprocess and whose processing cost is inexpensive since it has a complicated structure in its inside, and formed using a chemical-resistant material since it holds a pretreated sample and a staining solution in its inside. For example, the main body 15 is constituted by polypropylene, polyethylene terephthalate, polycarbonate, polystyrene, acrylonitrile butadiene styrene resin, or polymethyl methacrylate. The passage member 172 is preferably formed using the same material as that of the main body 15.

(F) Example of Step of Counting Number of Viable Bacteria

Examples when the number of viable bacteria in a food-derived sample counted using the microorganism-testing apparatus 1 according to the present embodiment will be describe below. The step of counting viable bacteria using the microorganism-testing chip 10 is shown in a flowchart in FIG. 12.

First, the configuration of the microorganism-testing chip 10 will be described once more using FIG. 13. The microorganism-testing chip 10 comprises the sample vessel 151 for holding the sample 1511, the microorganism-staining solution vessel 152 for holding the staining solution (reagent solution) 1521 for staining a microorganism in the sample, a food residue-removing section 160 as a filter for removing the food residue contained in the sample, the microorganism detection passage 173 for observing the fluorescence of the microorganism generated by the irradiation of an excitation light from an external light source, the detection solution discarding vessel 156 for discarding a mixture of the sample 1511 and the microorganism-staining solution 1521 having passed through the microorganism detection passage 173, solution passages 1571 to 1573 for providing connections between the sample vessel 151, the food residue-removing section 160, the microorganism-staining solution vessel 152, and the microorganism detection passage 173 and flowing the sample 1511 and the mixture, the vents 1591 to 1593 for supplying high-pressure gas or opening to the atmosphere to flow the sample 1511 and the mixture in the vessels, and the ventilation passages 1581 to 1583 for connecting the vessels to the vents 1591 to 1593.

In the following description, the solution passages 1571 to 1573, the vents 1591 to 1593, and the ventilation passages 1581 to 1583 are called a sample vessel—microorganism-staining solution vessel passage 1571, a microorganism-staining solution vessel—microorganism detection passage passage 1572, a microorganism detection passage—detection solution discarding vessel passage 1573, a sample vessel vent 1591, a microorganism-staining solution vessel vent 1592, a detection solution discarding vessel vent 1593, a sample vessel ventilation passage 1581, a microorganism-staining solution vessel ventilation flow passage 1582, and a detection solution discarding vessel ventilation flow passage 1583 based on the names of connected vessels except for being collectively represented.

The sample vessel 1511, the food residue-removing section 160, the microorganism-staining solution vessel 152, the microorganism detection passage 173, and the detection solution discarding vessel 156 are connected in series through the solution passages 1571 to 1573.

In FIG. 13, the solution passages 1571 to 1573 are each formed to a depth and passage width of, for example, 10 μm to 1 mm; the ventilation passages 1581 to 1583 are each formed to a depth and passage width of, for example, 10 μm to 1 mm; and the solution passages 1571 to 1573 are each formed so as to have a sectional area larger than that of each of the ventilation passages 1581 to 1583.

The microorganism-staining solution 1521 is enclosed in the microorganism-testing chip 10 in advance. The sample 1511 is injected into the sample vessel 151 through the vent 1591 before testing (S901).

The sample vessel 151 has a volume larger than that of the sample 1511. The microorganism-staining solution vessel 152 has a volume larger than the total volume of the sample 1511 and the microorganism-staining solution 1521. The sample vessel—microorganism-staining solution vessel passage 1571 is formed so as to have a highest point higher than the water level of the sample 1511 in the sample vessel 151. Similarly, the microorganism-staining solution vessel—microorganism detection passage passage 1572 is formed so as to have a highest point higher than the water level of the mixture of the sample 1511 and the microorganism-staining solution 1521.

The sample 1511 used here is obtained by adding saline in a mass ratio of 10 times the amount of the food to be tested and subjecting the mixture to stomaching treatment, followed by adding glycerin to a final concentration of 10%.

The microorganism-staining solution is a mixture of one type of a killed bacteria-staining solution for staining killed bacteria, two types of V/K bacteria-staining solutions for staining V/K bacteria, and a mitochondria-staining solution for staining mitochondria; the killed bacteria-staining solution uses, for example, an orange-colored cyanine fluorochrome for killed bacteria (final concentration: 0.01 $\mu$M to 10 $\mu$M), the V/K bacteria-staining solution uses a blue cyanine fluorochrome for V/K bacteria (final concentration: 0.01 $\mu$M to 10 $\mu$M) and LDS751 (final concentration: 0.1 $\mu$g/ml to 1 mg/ml), and the mitochondria-staining solution uses a red fluorochrome for mitochondria (final concentration: 0.01 $\mu$M to 10 $\mu$M).

Figure 12:
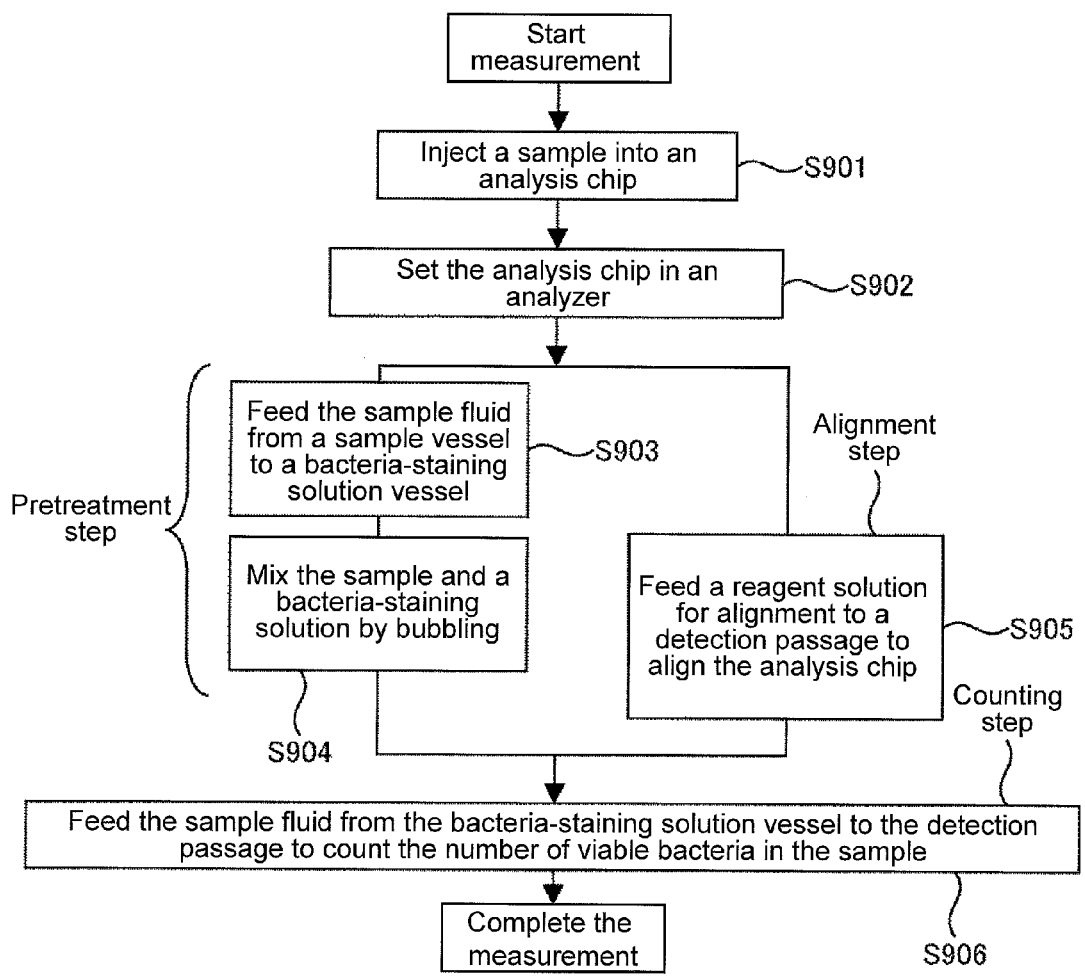
FIG. 12 is a diagram describing an analysis step in the microorganism-testing apparatus according to the embodiment of the present invention.

As shown in FIG. 12, the measurement of the number of viable bacteria using the microorganism-testing chip 10 is started in a state in which the microorganism-testing chip 10 is set in a microorganism-testing apparatus (analyzer) 1 (S902). This measurement step is composed of an alignment step of aligning the microorganism-testing chip 10 (S905), a pretreatment step of removing the food residue from a sample and staining microorganisms in the sample (S903 to S904), and a counting step of actually counting viable bacteria (S906).

The alignment step (S905) and the pretreatment step (S903 to S904) are performed in parallel since they are independent steps, and the counting step (S906) is carried out in the stage in which the former two steps have ended.

The alignment step (S905) is a general procedure for alignment. The step may be carried out to flow a reagent for alignment containing fluorescent microparticles providing an indicator into the microorganism detection passage 173 and use fluorescence emitted by the fluorescent microparticle as a guide, or may be performed to use a method as described in JP Application No. 2009-109153 as earlier filed by the present applicant. In the former case, the microorganism-testing chip 10 is provided with a vessel for holding the reagent for alignment (the diagrammatic representation is abbreviated). In the latter case, the microorganism detection passage 173 is irradiated with the excitation light 113 outputted from the excitation light source 111 to detect the amount of scattered light generated from the microorganism detection passage 173 and the amount of fluorescence generated from the microorganism-detecting section 17 to obtain the relationship of each amount to the movable position of the X-Y movable stage 125 as a profile. The detector 11 also movably controls the X-Y movable stage 125 based on the obtained profile to adjust the microorganism-testing chip 10 (specifically, the microorganism detection passage 173) to a position suitable for detection. Specifically, alignment in the X direction is carried out based on a change in the intensity of scattered light from the microorganism detection passage, and alignment in the Y direction is performed based on a change in the intensity of fluorescence amount generated from the microorganism-detecting section. The alignment in the X direction is first carried out and the alignment in the Y direction is then performed. In the alignment in the X direction, the detector 11 stocks the profile between the displacement in the X direction and the amount of the detected scattered light in the system unit 18 and moves the center of the microorganism detection passage 173 to the position at which the amount of the scattered light reaches the maximum level. In the alignment in the Y direction, the detector 11 stocks the profile between the displacement in the Y direction and the amount of the detected fluorescence in the system unit 18 and moves the center of the microorganism detection passage 173 to the position at which the amount of the fluorescence reaches the maximum level. When the distance between the center of the microorganism detection passage 173 here and the focus of the excitation light 113 is A, the detector 11 moves the microorganism detection passage 173 to the position corrected for the distance A to accurately focus the excitation light 113 on the center of the microorganism detection passage 173.

The movement of each solution in each step will be then described. In the pretreatment step, the sample 1511 is first moved to the microorganism-staining solution vessel 152 (S903). In this pretreatment step, pressure from the pressure-supply unit 14 is applied to the sample vessel 151 via the vent 1591. This increases atmospheric pressure in the sample vessel 151. Simultaneously, the internal pressure of the microorganism-staining solution vessel 152 is opened to the atmospheric pressure via the microorganism-staining solution vessel vent 1592. The sample 1511 enters the microorganism-staining solution vessel 152 owing to the difference in air pressure and is mixed with the microorganism-staining solution 1521.

Bubbling is used for mixing (S904). The bubbling applies pressure from the pressure-supply unit 14 to the vent 1593 and increases the air pressure in the detection solution discarding vessel 156 within the range lower than that in the sample vessel 151. Simultaneously, the sample vessel 151 and the microorganism-staining solution vessel 152 are opened to the atmosphere via the vents 1591 and 1592. Air flows into the microorganism-staining solution vessel 152 from the detection solution discarding vessel 156 through the microorganism detection passage 173. The air is converted to bubbles, and agitates the mixture when rising from the bottom of the mixture to its top to promote mixing.

Killed bacteria in the sample 1511 are stained with the killed bacteria-staining solution (where an orange-colored cyanine fluorochrome for killed bacteria (peak wavelength: 570 nm) is used) and the V/K bacteria-staining solution (where a blue cyanine fluorochrome for V/K bacteria (peak wavelength: 450 nm) and LDS751 (peak wavelength: 710 nm) are used), while viable bacteria in the sample 1511 are stained only with the V/K bacteria-staining solution.

The water level of the mixture of the two solutions does not exceed the highest point of the microorganism-staining solution vessel—microorganism detection passage passage 1572 connecting the microorganism-staining solution vessel 152 to the microorganism detection passage 173, and further the air contained in the microorganism-staining solution vessel 152 is emitted to the outside via the microorganism-staining solution vessel vent 1592. Because the air pressure in the microorganism-staining solution vessel 152 is equal to the atmospheric pressure, the mixture of the two solutions are not pressed out to the microorganism detection passage 173 and can be held in the microorganism-staining solution vessel 152 during a time necessary for reaction.

At this time, for the purpose of preventing flow into the microorganism detection passage 173, pressure from the pressure-supply unit 14 may be applied to the vent 1593 to increase the air pressure in the detection solution discarding vessel 156 within the range lower than that in the sample vessel 151.

During staining, it is desirable to keep the temperature of the microorganism-testing chip 10 constant to reduce effects of temperature change on staining.

When the sample 1511 flows into the microorganism-staining solution vessel 152 through the food residue-removing section 160, the food residue in the sample 1511 is removed from the sample 1511 by the food residue-removing section 160.

Now the pretreatment step is completed. The alignment of the microorganism-testing chip 10 is performed in parallel with the pretreatment.

When the above operation is completed, the mixture of the sample 1511 and the microorganism-staining solution 1521 is moved to the microorganism detection passage 173 to count viable bacteria in the sample (S906). In this step, pressure from the pressure-supply unit 14 is applied to the sample vessel 151 through the vent 1591. This increases the air pressure in the sample vessel 151. Simultaneously, the internal pressure of the microorganism-staining solution vessel 152 is opened to the atmospheric pressure via the microorganism-staining solution vessel vent 1592. The sample 1511 enters the microorganism-staining solution vessel 152 owing to the difference in air pressure and is mixed with the microorganism-staining solution 1521. Pressure from the pressure-supply unit 14 is applied through the vent 1592 to increase the air pressure in the microorganism-staining solution vessel 152. Simultaneously, the detection solution discarding vessel 156 is opened to the atmosphere via the vent 1593. The other vent 1591 is closed. Owing to the difference in air pressure, the mixture flows from the microorganism-staining solution vessel 152 through the microorganism detection passage 173 into the detection solution discarding vessel 156.

Bacterial cells in the mixture are counted when they pass through the microorganism detection passage 173. The counting of bacterial cells in the microorganism detection passage 173 is carried out using a fluorescence flow cytometry method. In FIG. 13, the excitation light 113 is irradiated from the direction normal to the paper plane. Thus, from the microorganisms, fluorescence from the pigment with which the microorganisms are stained and scattered light from the microorganisms occur, and from food-derived particles such as chloroplasts and chromatophores, fluorescence from the pigment adsorbing to the food-derived particles, the autofluorescence of food-derived materials, and scattered light from the particles occur. The details of these fluorescences are as shown in FIG. 8, enabling the discrimination among viable bacteria, killed bacteria, and food-derived materials. Because the amount of scattered light varies depending on the size of bacterial cells or particles, the size of bacterial cells or particles can also be determined.

(G) Example of Configuration of Detector

An example of the configuration of the detector 11 constituting the microorganism-testing apparatus 1 will now be described with reference to FIG. 14. The detector 11 of the present embodiment is suitable for counting viable bacteria in a food-derived sample. Thus, use of the detector 11 can discriminate between viable bacteria and killed bacteria. The optical system for the detector may be different between the excitation spectrum of a fluorochrome and the fluorescence spectrum thereof. Here, the case of using an orange-colored cyanine fluorochrome for killed bacteria (peak wavelength: 570 nm) as a killed bacteria-staining solution, a blue cyanine fluorochrome for V/K bacteria (peak wavelength: 450 nm) and LDS751 (peak wavelength: 720 nm) as a V/K bacteria-staining solution, and a red fluorochrome for mitochondria (peak wavelength: 640 nm) as a staining solution for mitochondria will be described.

Figure 14:
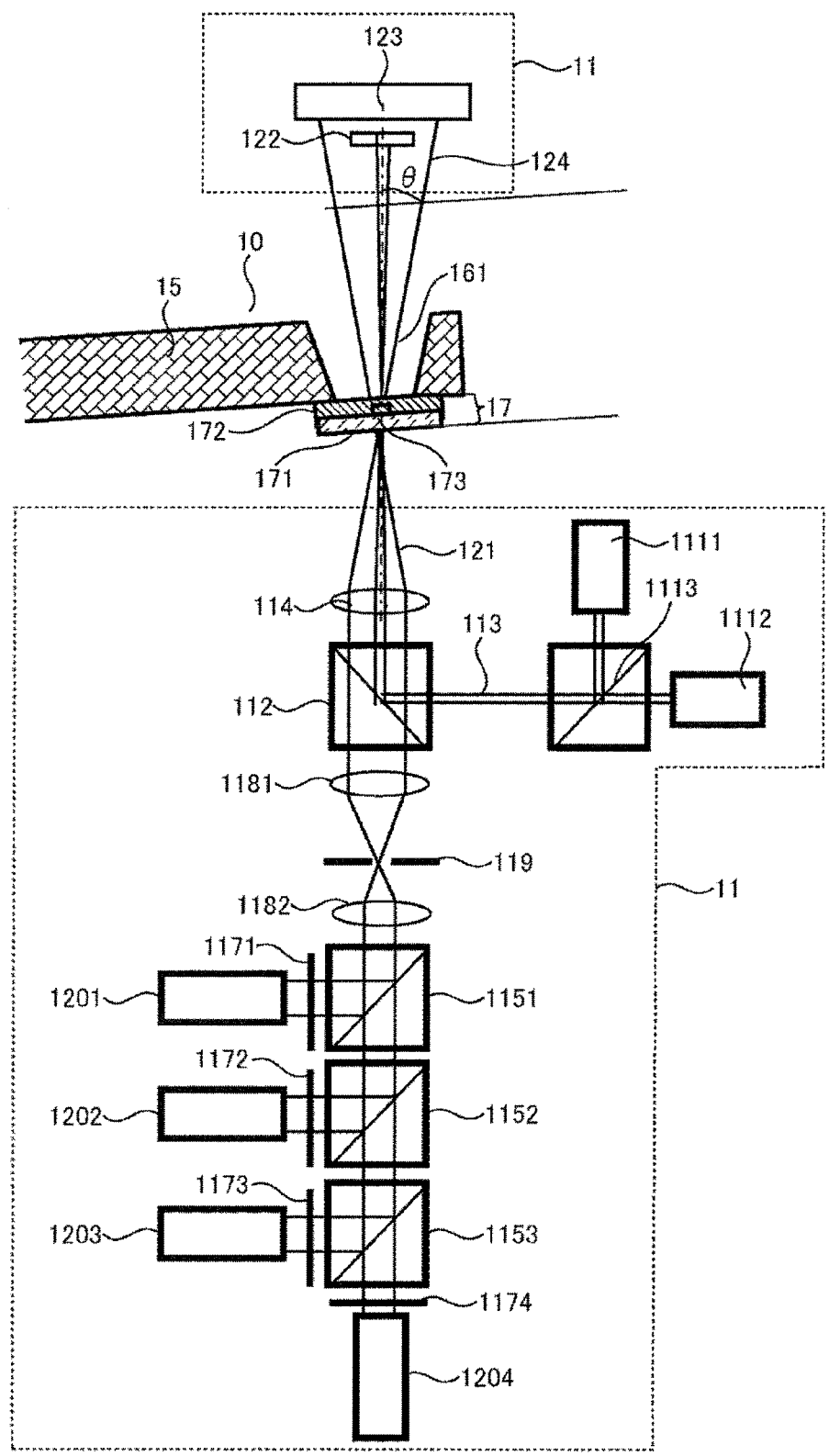
FIG. 14 is a drawing showing an example of a skeleton framework of a detector mounted in the microorganism-testing apparatus according to the embodiment of the present invention.

The optical system of the detector 11 in FIG. 14 is configured to be suitable when 4 types of fluorochromes are used. Of course, when 5 or more types of fluorochromes are used, an optical system is provided according to the pigments.

The excitation light source 111 in the detector 11 has a blue light source for excitation 1111 (wavelength: 405 nm), a green light source for excitation 1112 (wavelength: 532 nm), and a dichroic mirror for synthesis of light sources 1113 for synthesizing the blue light source for excitation 1111 and the green light source for excitation 1112. To detect scattered light, the detector 11 also has the scattered light detector 123 for detecting scattered light 124 from microorganisms flowing through the microorganism detection passage 173 and the baffle 122 for preventing the excitation light 113 from the excitation light source 111 from directly entering the scattered light detector 123. To detect fluorescence, the testing apparatus also has a dichroic mirror for separating excitation light and fluorescence 112, reflecting excitation light 113 and passing fluorescence from the microorganisms, the objective lens 114 for condensing the fluorescence from microorganisms and food-derived particles flowing through the microorganism detection passage 173 to make parallel light, a condensing lens 1181 for condensing parallel light, the pinhole 119 used as a space filter for cutting stray light, a lens 1182 for converting back into parallel light, a dichroic mirror for separating blue fluorescence 1151, reflecting light having a wavelength of 480 nm or less and passing light having a wavelength of 480 nm or more, a band-pass filter for blue fluorescence 1171, passing only light having a wavelength of near 450 nm, a dichroic mirror for separating orange-colored fluorescence 1152, passing light having a wavelength of 600 nm or more, a band-pass filter for orange-colored fluorescence 1172, passing only light having a wavelength of near 570 nm, a dichroic mirror for separating red fluorescence 1153, passing light having a wavelength of 680 nm or more, a band-pass filter for red fluorescence 1171, passing only light having a wavelength of near 640 nm, a band-pass filter for near-infrared fluorescence 1174, passing only light having a wavelength of near 720 nm, a photodetector for blue fluorescence 1201, detecting fluorescence passing through the band-pass filter for blue fluorescence 1171, a photodetector for orange-colored fluorescence 1202, detecting fluorescence passing through the band-pass filter for orange-colored fluorescence 1172, a photodetector for red fluorescence 1203, detecting fluorescence passing through the band-pass filter for red fluorescence 1173, and a photodetector for near-infrared fluorescence 1204, detecting fluorescence passing through the band-pass filter for near-infrared fluorescence 1174.

Laser light sources are used as the blue light source for excitation 1111 and the green light source for excitation 1112; a photodiode is used as the photodetector for scattered light; and photomultipliers (PMT) are used as the photodetector for blue fluorescence 1201, the photodetector for orange-colored fluorescence 1202, the photodetector for red fluorescence 1203, and the photodetector for near-infrared fluorescence 1204. As described above, the alignment of the microorganism detection passage 173 in the microorganism-testing chip 10 has been completed. Thus, the microorganism detection passage 173 in the microorganism-testing chip 10 is disposed at the position of the focus of the objective lens 114.

Excitation lights (wavelengths: 405 nm and 532 nm) outputted from the blue light source for excitation 1111 and the green light source for excitation 1112 are reflected by the dichroic mirror for separating excitation light and fluorescence 112, thereby change their traveling direction, and are irradiated on the microorganism detection passage 173. The irradiation excites the orange-colored cyanine fluorochrome for killed bacteria, the blue cyanine fluorochrome for V/K bacteria and LDS751 with which microorganisms flowing through the microorganism detection passage 173 are stained, the red fluorochrome for mitochondria with which mitochondria are stained, chloroplasts, and chromatophores. Fluorescents from the orange-colored cyanine fluorochrome for killed bacteria (peak wavelength: 570 nm), the blue cyanine fluorochrome for V/K bacteria (peak wavelength: 450 nm), LDS751 (peak wavelength: 720 nm), and the red fluorochrome for mitochondria (peak wavelength: 640 nm) and autofluorescences (560 nm to 700 nm) of chloroplasts and chromatophores enter the objective lens 114.

Fluorescence from the blue cyanine fluorochrome for V/K bacteria is reflected by dichroic mirror for separating blue fluorescence 1151, passes through the band-pass filter for blue fluorescence 1171, and then enters the photodetector for blue fluorescence 1201. Fluorescence from the orange-colored cyanine fluorochrome for killed bacteria and a portion of autofluorescence of chromatophores are reflected by dichroic mirror for separating orange-colored fluorescence 1152, pass through the band-pass filter for orange-colored fluorescence 1172, and then enter the photodetector for orange-colored fluorescence 1202. Fluorescence from the red fluorochrome for mitochondria, autofluorescence of chloroplasts, and a portion of autofluorescence of chromatophores are reflected by the dichroic mirror for separating red fluorescence 1153, pass through the band-pass filter for red fluorescence 1173, and then enter the photodetector for red fluorescence 1203. Fluorescence from the V/K bacteria-staining solution LDS751 passes through the dichroic mirror for separating red fluorescence 1153 and the band-pass filter for near-infrared fluorescence 1174 and then enters the photodetector for near-infrared fluorescence 1204. Fluorescences derived from 4 types of pigments can be thus separated based on the difference in the wavelength.

Excitation lights outputted from the blue light source for excitation 1111 and the green light source for excitation 1112 impinge on microorganisms flowing through the microorganism detection passage 173 to generate the scattered lights 124. The amount of scattered light varies depending on the size of fine particles, thereby enabling the measurement of the size of the fine particles. Obtaining measurement information on the size of fine particles further improves the accuracy of discrimination between microorganisms and contaminants such as food residues.

Fluoresences detected by the photodetector for blue fluorescence 1201, the photodetector for orange-colored fluorescence 1202, the photodetector for red fluorescence 1203, and the photodetector for near-infrared fluorescence 1204 and scattered light detected by the photodetector for scattered light 123 are each converted to an electric signal and then sent to the system unit 18 (FIG. 10). The system unit 18 processes electric signals sent from the photodetector for blue fluorescence 1201 as a photodetector for short wavelength, the photodetector for orange-colored fluorescence 1202 as a photodetector for long wavelength, and the photodetector for scattered light 123, and outputs information on the number of microorganisms as a result of testing to the output unit 19 (FIG. 10).

Meanwhile, the excitation lights 113 from the blue light source for excitation 1111 and the green light source for excitation 1112 can be partly reflected on the surface of the microorganism-detecting section 17 and return to the detector 11. To prevent the reflection, it is desirable that the normal vector of the microorganism-detecting section 17 be not parallel to the optical axis of the excitation light 113. Thus, the angle α between the normal vector of the microorganism-detecting section 17 and the optical axis of the excitation light 113 is preferably 10 to 20°. FIG. 14 represents an example of such mounting.

In FIG. 14, the angle formed by the surface of the microorganism-detecting section 17 and the optical axis of the excitation light 113 is denoted as θ(θ+α=90°). θ is less than 90 degrees; however, it is set so that the excitation light 113 is not totally reflected on the surface of the microorganism-detecting section 17. θ may be 80 to 70°. The microorganism-detecting section 17 is inclined so that the normal vector of the microorganism-detecting section 17 be not parallel to the optical axis of the excitation light 113; however, the excitation light is irradiated from the direction normal to the microorganism detection passage 173.

All publications, patents, and patent applications cited herein are incorporated herein by reference in their entirety.

What is claimed is:

1. A method for testing cells or microorganisms, comprising multiply staining the cells or microorganisms with two membrane-permeable fluorochromes whose fluorescence amounts are amplified by binding to a nucleic acid and one membrane-impermeable fluorochrome whose fluorescence amount is amplified by binding to a nucleic acid, simultaneously irradiating a plurality of excitation lights having different specific peak wavelengths on a sample fluid containing the multiply stained cells or microorganisms, measuring fluorescences emitted from the irradiated sample fluid using fluorescence cytometry, detecting the cells or microorganisms in the irradiated sample fluid based on the fluorescences emitted from the cells or microorganisms, and discriminating between the multiply stained cells or microorganisms and particles formed by self-aggregation of the membrane-permeable fluorochromes or the membrane-impermeable fluorochromes wherein objects emitting a plurality of fluorescences derived from the two membrane-permeable fluorochromes are determined to be the multiply stained cells or microorganisms, and objects emitting single fluorescence are determined to be the particles formed by aggregation of the flurochromes, and
   wherein a membrane-permeable fluorochrome which has a fluorescence spectrum peak at less than 550 nm and a membrane-permeable fluorochrome which has a fluorescence spectrum peak at 680 nm or more are used as the two membrane-permeable fluorochromes, and a membrane-impermeable fluorochrome which has a fluorescence spectrum peak at 550 nm or more and less than 680 nm is used as the one membrane-impermeable fluorochrome to multiply stain the cells or microorganisms.

2. The method for testing cells or microorganisms according to claim 1, wherein the two membrane-permeable fluorochromes and the one membrane-impermeable fluorochrome have peaks of fluorescence spectra 50 nm or more away from each other.

3. A method of testing cells or microorganisms, comprising steps of:
   multiply staining the cells or microorganisms with two membrane-permeable fluorochromes whose fluorescence amounts are amplified by binding to a nucleic acid and one membrane-impermeable fluorochrome whose fluorescence amount is amplified by binding to a nucleic acid, wherein a membrane-permeable fluorochrome which has a fluorescence spectrum peak at less than 550 nm and a membrane-permeable fluorochrome which has a fluorescence spectrum peak at 680 nm or more are used as the two membrane-permeable fluorochromes, and a membrane-impermeable fluorochrome which has a fluorescence spectrum peak at 550 nm or more and less than 680 nm is used as the one membrane-impermeable fluorochrome;

simultaneously irradiating a plurality of excitation lights having different specific peak wavelengths on a sample fluid containing the multiply stained cells or microorganisms;

measuring fluorescences emitted from the irradiated sample fluid using fluorescence cytometry;

detecting the multiply stained cells or microorganisms based on the fluorescences emitted from the cells or microorganisms in the irradiated sample fluid; and discriminating between objects emitting a plurality of fluorescences derived from the two membrane-permeable fluorochromes and objects emitting single fluorescence, wherein the objects emitting a plurality of fluorescences are the multiply stained cells or microorganisms, and the objects emitting single fluorescence are particles formed by self-aggregation of the fluorochromes.

4. The method for testing cells or microorganisms according to claim 3, wherein the two membrane-permeable fluorochromes and the one membrane-impermeable fluorochrome have peaks of fluorescence spectra 50 nm or more away from each other.

\* \* \* \* \*